(12) United States Patent
Gordon

(10) Patent No.: US 9,163,234 B2
(45) Date of Patent: Oct. 20, 2015

(54) CULTURE METHOD

(75) Inventor: Myrtle Gordon, Binfield (GB)

(73) Assignee: Omnicyte Limited, London (GB)

( * ) Notice: Subject to any disclaimer, the term of this patent is extended or adjusted under 35 U.S.C. 154(b) by 269 days.

(21) Appl. No.: 13/877,579

(22) PCT Filed: Oct. 6, 2011

(86) PCT No.: PCT/GB2011/051914
§ 371 (c)(1),
(2), (4) Date: Apr. 24, 2013

(87) PCT Pub. No.: WO2012/046065
PCT Pub. Date: Apr. 12, 2012

(65) Prior Publication Data
US 2013/0217125 A1    Aug. 22, 2013

(30) Foreign Application Priority Data

Oct. 6, 2010  (GB) ................................ 1016856.5
Oct. 6, 2010  (GB) ................................ 1016857.3
Dec. 16, 2010 (GB) ................................ 1021435.1

(51) Int. Cl.
| | |
|---|---|
| *C12N 5/02* | (2006.01) |
| *C12N 5/00* | (2006.01) |
| *C12N 15/113* | (2010.01) |
| *C12N 5/0789* | (2010.01) |
| *C12N 5/0775* | (2010.01) |
| *C12N 5/074* | (2010.01) |

(52) U.S. Cl.
CPC ............ *C12N 15/113* (2013.01); *C12N 5/0647* (2013.01); *C12N 5/0675* (2013.01); *C12N 5/0696* (2013.01); *C12N 2500/90* (2013.01); *C12N 2500/99* (2013.01); *C12N 2501/125* (2013.01); *C12N 2501/2301* (2013.01); *C12N 2501/2303* (2013.01); *C12N 2501/2306* (2013.01); *C12N 2501/605* (2013.01); *C12N 2501/65* (2013.01)

(58) Field of Classification Search
None
See application file for complete search history.

(56) References Cited

U.S. PATENT DOCUMENTS

2007/0243171 A1    10/2007    Bunce
2013/0217125 A1*   8/2013     Gordon ................. 435/377

FOREIGN PATENT DOCUMENTS

| | | |
|---|---|---|
| WO | WO-02/086104 A1 | 10/2002 |
| WO | WO-03/055989 A2 | 7/2003 |
| WO | WO-2005/046596 A2 | 5/2005 |
| WO | WO-2005059113 A1 | 6/2005 |
| WO | WO-2008070082 A2 | 6/2008 |

OTHER PUBLICATIONS

European Patent Office International Search Report and Written Opinion of the International Searching Authority for PCT/GB2011/051914 mailed May 7, 2012 (18 pages).
Li, Qi-Jing et al., "miR-181a is an Intrinsic Modulator of T Cell Sensitivity and Selection," Apr. 6, 2007 Cell, vol. 129 (pp. 147-161).
Kane, Nicole M. et al., "A Role for microRNAs 99b, 181a and 181b in the Differentiation to Vascular Endothelial Cells from Human Embryonic Stem Cells," Jan. 1, 2012 Stem Cells, XP055016957 (22 pages).
Chen, Chang-Zheng et al., "MicroRNAs Modulate Hematopoietic Lineage Differentiation," Jan. 2, 2004, Science, vol. 303 (pp. 83-86).
Choong, Meng-Ling et al., "MicroRNA expression profiling during human cord blood-derived CD34 cell erythropoiesis," Mar. 28, 2007 Experimental Hematology, vol. 35, No. 4 (pp. 551-564).
Xu, Na et al., "MicroRNA-145 Regulated OCT4, SOX2, and KLF4 and Represses Pluripotency in Human Embryonic Stem Cells," May 15, 2009 Cell, vol. 137 (pp. 647-658).
Bontkes, Hetty J. et al., "Expansion of Dendritic cell precursors from human Cd 34+ progenitor cells isolated from healthy donor blood; growth factor combination determines proliferation rate and functional outcome," Aug. 2002, Journal of Leukocyte Biology, vol. 72 (pp. 321-329).
Kanold, J. et al., "Neuroblastoma Ex vivo expansion of autologous PB CD34+ cells provides a purging effect in children with neuroblastoma," 2003 Bone Marrow Transplantation, vol. 32, (pp. 485-488).
Nagaoka, Masato et al., "Culture of human pluripotent stem cells using completely defined conditions on a recombinant E-cadherin substratum," 2010 BMC Developmental Biology, vol. 10, No. 60 (12 pgs.).
Totonchi, Mehdi et al., "Feeder- and serum-free establishment and expansion of human induced pluripotent stem cells," 2010 Int. J. Dev. Biol., vol. 54 (pp. 877-886).
Colter, David C. et al., "Rapid expansion of recycling stem cells in cultures of plastic-adherent cells from human bone marrow," Mar. 28, 2000, PNAS, vol. 97, No. 7 (pp. 3213-3218).
Gordon, Myrtle Y. et al., "Characterization and Clinical Application of Human CD34+ Stem/Progenitor Cell Populations Mobilized into the Blood by Granulocyte Colony-Stimulating Factor," 2006 Stem Cells, vol. 24 (pp. 1822-1830).

* cited by examiner

*Primary Examiner* — Michael Burkhart
(74) *Attorney, Agent, or Firm* — Harris Beach PLLC

(57) ABSTRACT

The invention provides methods of culturing cells, particularly maintaining the differentiation potential of a population of cells with differentiation potential. The methods involve contacting cells with an inhibitor of miRNA-181a* and/or incubation in a serum-free medium. A serum-free medium is also provided. Also provided are progeny stem cells, methods of obtaining them, and uses thereof.

21 Claims, 17 Drawing Sheets

Best overall match at the Nanog 3'UTR

```
              A      G C        U     C
Nanog 3'UTR:  GUGCAGU G GCGGUC  UGG
  miR-181a*:  CAUGUUA U UGCCAG  ACC
              C       G         CU    A
```

CULTURE METHOD

CROSS-REFERENCE TO RELATED APPLICATIONS

This application is a national stage application under 35 U.S.C. §371 of PCT Application No. PCT/GB02011/051914, filed Oct. 6, 2011, which claims priority to and the benefit of GB patent applications GB1016856.5, filed on Oct. 6, 2010, GB1016857.3, filed on Oct. 6, 2010 and GB1021435.1, filed on Dec. 16, 2010, each of which applications is incorporated herein by reference in its entirety.

The present invention relates to the field of stem cell culture. More particularly, the present invention relates to a method of culturing a population of cells with differentiation potential and to a method of maintaining the differentiation potential of a population of cells. The present invention also relates to a medium for stem cell culture, as well as to a new population of stem cells and uses thereof.

Cells with differentiation potential, i.e. cells which are pluripotent, multipotent or totipotent, are collectively termed "stem cells". Stem cells can differentiate into new, different cell types. Stem cells are of increasing commercial, therapeutic and academic importance. They can, for instance, potentially be used to repair damage to any tissue in the body and therefore have immense potential for all types of regenerative medicine.

Stem cells are present in all body tissues and organs but some, like bone marrow and blood, are more accessible than others, like liver and brain. However, stem cells exist in very small numbers in marrow and blood, and need to be extracted and then cultured to increase the number of viable cells before they can be used clinically. Currently, many attempts are being made to accomplish the aim of providing stem cells in sufficient numbers to perform tissue-specific stem cell transplantation.

In recent years, great progress has been achieved in stem cell research. Studies in embryonic and somatic (adult) stem cell research have provided basic insight into the molecular and cellular biology of stem cell development. It is recognised that pluripotent stem cells such as embryonic stem cells can replenish differentiated cell types and achieve long-term tissue reconstitution. Like embryonic stem cells, adult stem cells have the capacity for self-renewal and multi-lineage differentiation properties. Adult stem cells are present in approximately 1-2% of the total cell population within a specific tissue and are essential in the maintenance of local tissue homeostasis. These cells are usually quiescent and are held in an undifferentiated state within their niche until they receive a signal to differentiate. They reside in various tissue types including the bone marrow, brain, digestive system, skin, retina, muscles, pancreas, and liver.

Hematopoietic stem cells (HSC), which sustain the formation of the blood and immune systems, are the most widely studied and best characterised adult stem cells. These stem cells can be found in bone marrow along with mesenchymal stem cells (MSC). It was previously thought that adult stem cells were lineage restricted; however, recent studies have shown that HSC and MSC have enormous plasticity which makes them attractive for stem cell-based therapeutic development. In addition, there are several advantages to exploiting adult stem cells for therapeutic applications, including ease of manipulation and procurement, and a lack of serious ethical issues. Most importantly, adult stem cells (autologous donor) are non-immunogenic and therefore reduce the chance of rejection.

Methods of providing and culturing stem cells, are therefore required. Stem cells are present in all body tissues and organs but some, like bone marrow and blood, are more accessible than others, like liver and brain. However, stem cells exist in very small numbers in marrow and blood, and need to be extracted and then expanded before they can be obtained in useful quantities. Currently, many attempts are being made to accomplish the aim of providing stem cells in sufficiently useful numbers, for instance to perform tissue-specific stem cell transplantation.

Various methods of culturing stem cells are known in the art. For instance Himburg et al., (2010) Pleiotrophin regulates expansion and regeneration of haemopoietic stem cells *Nat med* 16(4): 475-82 and Delaney et al., (2010) Notch-mediated expansion of human cord blood progenitor cells capable of myeloid reconstitution *Nat med* 16(2):232-6.

Efforts have focused on the bone marrow as a source of stem cells. WO2005/059113 discloses a particularly advantageous type of pluripotent stem cell. This stem cell can be directly isolated from bone marrow and/or blood, e.g. peripheral blood, or from material taken from the umbilical cord, and has the unique ability to differentiate into ectodermal, mesodermal and endodermal cells. These cells are thus clearly multipotent or pluripotent, if not totipotent. Therefore, the stem cells described in WO2005/059113 provide a useful source of cells for tissue transplantation that may be used in an autologous (self-to-self) manner.

The cells disclosed in WO2005/059113 are known in the art as "OmniCytes".

WO 2005/059113 discloses the culture of OmniCytes using medium containing serum (Examples 2 and 9 of WO 2005/059113). More particularly, WO 2005/059113 discloses overlaying OmniCytes with methylcellulose containing serum and cytokines G-CSF (100 ng/ml), GM-CSF (1 ng/ml), IL-3 (5 ng/ml) and SCF (20 ng/ml). WO 2005/059113 reports that under these conditions, a heterogeneous population of cells is obtained (Example 2). Example 9 of WO 2005/059113 explains that the OmniCytes divide and self-renew to form colonies of adherent stem cells, but they also give rise to adherent cells that exhibit morphologies characteristic of mesenchymal, epithelial, vascular and neural cell types. In addition, non-adherent cells are released into the methylcellulose where large colonies of haemopoietic cells form.

Thus, WO 2005/059113 fails to teach a reliable method of culturing stem cells, because spontaneous differentiation takes place. This document highlights the difficulties associated with trying to culture OmniCytes, and these difficulties are associated with the culture of any stem cells, because cell death and/or spontaneous differentiation typically takes place. The present inventors also found that when using the culture method of WO 2005/059113, significant cell death occurred, so that after about 28 days of culture, substantially all of the cells were dead.

When culturing populations of stem cells, expansion of the population is often desired in order to obtain sufficient cell numbers for the desired purpose. A major problem when culturing stem cells is that, over time, the cells have a tendency to differentiate. Cells which have differentiated possess less differentiation potential than cells which have not yet differentiated, i.e. they are less multipotent or have less "sternness". In other words, over time, cultured cells have a tendency to lose differentiation potential, the very property which characterises them as stem cells and makes them useful and desirable in certain methods. Thus, many known methods for expanding populations of stem cells have the disadvantage of resulting in a population of cells with a lower differentiation potential. There is therefore a need in the field to provide methods of culturing a population of cells with differentiation potential in which the tendency of the cells to differentiate is reduced, i.e. in which the differentiation potential of the population is maintained.

The differentiation potential of a population of cells can be determined by assessing the levels of known markers of differentiation potential, such as the pluripotency factors POU5F1, SOX2, MYC, NANOG and HoxB4. Alternatively, the differentiation potential of a population of cells can be determined by attempting to differentiate said cells into a variety of different cell types using known mediators of differentiation and assessing whether or not differentiation into the desired cell types has been possible, for instance by determining the presence or levels of cell type-specific markers. Alternatively, an alkaline phosphatase assay may be used to determine the differentiation state of a cell or population of cells, wherein a higher the level of alkaline phosphatase activity is indicative of a lower extent of cellular differentiation.

Prior art methods of stem cell culture traditionally involved the use of feeder cells, i.e. the stem cells were cultured in contact with a layer of feeder cells which secrete factors and can provide a growth substrate. As summarised in Nagaoka et al. (BMC Developmental Biology 2010, 10:60), given the safety concerns and contamination issues associated with the use of feeder cells, culture methods which do not require feeder cells have been developed, but such methods typically require the use of an extracellular matrix such as Matrigel. Matrigel is the trade name for a gelatinous protein mixture secreted by Engelbreth-Holm-Swarm (EHS) mouse sarcoma cells (available e.g. from BD Biosciences) which comprises a mixture of proteoglycans. Key components of Matrigel are structural proteins such as laminin. Growth factors including TGF-beta, epidermal growth factor, insulin-like growth factor, FGF and tissue plasminogen activator are also present.

Matrigel is relatively impure, comprises a fairly large number of different growth factors, and significant batch-to-batch variation can exist, so recently efforts have been made to develop simpler and more defined culture conditions for stem cells. Nagaoka et al. (supra) report the development of a recombinant E-cadherin substratum, which can support the growth of various pluripotent cells.

Conventionally, cells and particularly stem cells are cultured in media containing serum. Serum is a major source of metabolites, hormones, vitamins, iron, proteins, attachment factors such as fibronectin, and growth factors. Many cell culture methods depend on the use of serum, i.e. the omission of serum from the method has a significant detrimental effect. For example, the omission of serum may cause cell growth to slow down significantly or even result in cell death. The omission of serum may also alter the differentiation status of the cells, for example it may cause stem cells to differentiate spontaneously. In addition, serum acts as buffer against a variety of perturbation and toxic effects such as pH change, presence of heavy metal ions, proteolytic activity, or endotoxins. However, there are various disadvantages linked to the use of serum, mainly the batch to batch variability in its composition, its association with a higher contamination risk (for example, viral contamination), and the subsequent difficulties encountered in downstream processing (e.g. purification of the cells to get rid of the serum-proteins). It is therefore advantageous to avoid the use of serum, but as mentioned above, serum can typically not simply be omitted from a medium/method without affecting the status of the cells.

There remains a long felt-need for a culture medium and method for the culture of stem cells which avoids complex and undefined components such as feeder cells, serum or matrices such as Matrigel, and which contains a small number of defined factors which help to maintain the pluripotent state of the cell population.

DETAILED DESCRIPTION OF INVENTION

As set out in the Examples, the present inventors have identified that a particular miRNA molecule, miRNA-181a*, is up-regulated in cells without differentiation potential compared to in cells with differentiation potential. The present inventors have further identified the genetic target of this miRNA sequence and discovered that the miRNA sequence functions in the down-regulation of the expression of the sternness factor Nanog. The present inventors have further shown that inhibitors of this miRNA can be effective in reversing the effects of the miRNA, i.e. in up-regulating Nanog and leading to an expansion of cells with differentiation potential.

Thus, in one aspect the present invention provides a method of culturing a population of cells with differentiation potential, said method comprising contacting said cells with an inhibitor of miRNA-181a*.

Alternatively viewed, the present invention provides a method of maintaining the differentiation potential of a population of cells with differentiation potential, said method comprising contacting said cell cells with an inhibitor of miRNA-181a*.

The present inventors have developed a method for culturing stem cells in vitro. As set out in the Examples, they found that stem cells may be cultured in defined serum-free medium comprising Interleukin-3, Interleukin-6 and stem-cell factor (SCF). Under these conditions, culture for over 50 days and an increase in cell numbers by 4-5 logs was achieved. Preferably, Interleukin-1 is also present, which may increase cell culture. The serum-free medium of the invention is surprisingly better at enhancing proliferation and maintaining stem cell viability in culture than prior art media, for example the medium used in WO 2005/059113. Advantageously, it may be used in combination with an inhibitor of miRNA-181a*.

Thus, in another aspect, the present invention provides a serum-free medium suitable for culturing stem cells, said serum-free medium comprising Interleukin-3, Interleukin-6 and SCF. Preferably, said medium also contains Interleukin-1.

In another aspect, the present invention provides a method of culturing a population of cells with differentiation potential, said method comprising contacting said cells with serum free medium of the invention.

A method of culturing a population of cells is a method of incubating a population of cells under conditions suitable to keep the population alive. Thus, the above methods will typically comprise incubation of the population after initial contact with the inhibitor molecule and/or serum free medium.

The methods of the present invention are an effective, non-invasive, and safe alternative for culturing populations of cells with differentiation potential. In some embodiments, these methods achieve the up-regulation of Nanog via the down-regulation of miRNA-181a*. The methods lead to the culturing of the cells and at the same time reduce the loss of differentiation potential in the population of cells ordinarily encountered when culturing stem cells.

Preferably, according to the methods of the invention, cell proliferation takes place and most preferably, cell proliferation outweighs any cell death, leading to an increase in cell numbers, i.e. expansion of the population. Thus, the method of the invention preferably yields an increase in viable cell number.

The present methods typically comprise, after the initial contacting step, the incubation of the population of cells under conditions required and for as long as required for the desired number of cells to be obtained. The incubation may be carried out for at least 1, 2, 3, 4, 5, 6 or 7 days, e.g. 2-4 days, but it may also be carried out for at least 1, 2, 3 or 4 weeks, but preferably no more than about 5 weeks. The contacting with an inhibitor of MiRNA-181* step may be performed daily for at least one day, preferably at least two days, more preferably about three days. Preferably said contacting step is performed once, twice or thrice daily or every alternate day. The particular administration regimens to be used can be readily determined by one of ordinary skill in the art to suit his desired purpose, particular starting cell type and delivery method. By way of example, picoMolar concentrations of the single or double stranded RNA molecules discussed below may be used. Alternatively, each contacting step may comprise contacting about $1 \times 10^5$ cells with 10 to 500 mM, preferably 50 to 100 mM of inhibitor.

In the methods of the invention, the media may be removed after a suitable incubation time and replaced with new, i.e. fresh media. Preferably, the old media is removed and replaced with new media about every 7 days, e.g. every 6-8 or every 5-9 days, The media may be changed more frequently, e.g. about every 1, 2, 3, 4 or 5 days.

An increase in the number of cells in a population can be detected, for instance, by counting the number of cells before and after the culturing method is performed. Thus, cell culture may be assayed by counting total viable cells, for example using the trypan exclusion assay. Alternatively, the extent of expansion may be quantified via microscopic examination of the degree of confluency or by using a thymidine or BrdU incorporation assay.

Preferably the methods of the present invention are performed in vitro or ex viva.

The methods of the present invention are culture methods in which the differentiation potential of the population of cells is maintained. Over time, when culturing a population of cells, the cells have a tendency to differentiate. The present methods counter this tendency and so maintain the level of differentiation potential of the population of cells during culturing.

"Differentiation potential" is a qualitative measure of the potency of a cell or population of cells, i.e. it is a description of the ability of a cell or population of cells to differentiate into different types of cell. A totipotent cell can, in principle, give rise to any mature cell type. A pluripotent cell has a greater differentiation potential than a multipotent cell. Within a population of cells, individual cells may possess different differentiation potentials. Unless prevented, a population of multipotent cells may, after time or during culturing, comprise some cells which have differentiated into somatic cells and some cells which have not differentiated and are still multipotent. Similarly, a population of pluripotent cells, after time, may contain multipotent cells and somatic cells as well as pluripotent cells.

The present inventors have developed a method of culturing a population of cells with differentiation potential without incurring a significant loss in the differentiation potential of the population. Thus, they have provided a method of maintaining the differentiation potential of a population of cells with differentiation potential.

A "stem cell" is a cell capable of self-renewal, i.e. being able to make more stem cells by dividing, as well as being able to give rise to different cell types. The ability to give rise to different cell types is referred to as "potency". The stem cell may be totipotent, pluripotent or multipotent.

A "pluripotent" cell is a cell that has the potential to differentiate into any of the three germ layers: endoderm (e.g. interior stomach lining, gastrointestinal tract, the lungs), mesoderm (e.g. muscle, bone, blood, urogenital), or ectoderm (e.g. epidermal tissues and nervous system).

A "multipotent" cell is a cell which has the potential to give rise to cells from multiple, but a limited number of lineages.

A "somatic" cell is any type of cell forming the body of an organism with the exception of germ line cells (gametes), the cells from which gametes are made (gametocytes), multipotent cells and pluripotent cells. Typically, a somatic cell will be differentiated and thus committed to a particular lineage.

The cells cultured according to the methods of the present invention may be any type of stem cell, including adult stem cells, embryonic stem cells and carcinoma-derived stem cells, adult stem cells being preferred. The cells may include haematopoietic stem cells, mesenchymal stem cells and iPSCs (induced pluripotent stem cells).

Preferably, the population of cells are CD34+ cells. CD34+ cells are cells which express the antigen CD34, a glycoprotein marker found, but not exclusively so, on stem cells. Optionally the CD34+ cells are derived from umbilicus, bone marrow, liposuction sources, T-cells, fibroblasts, liver, pancreas and cells from blood vessels. Preferably the cells are haematopoietic stem cells.

More preferably, the population of cells is a population of OmniCytes. OmniCytes are disclosed in WO2005/059113, the content of which is incorporated here by reference. OmniCytes are adult, i.e. non-foetal, and can be directly isolated from bone marrow and/or blood, e.g. peripheral blood, or from material taken from the umbilical cord, and have the unique ability to differentiate into ectodermal, mesodermal and endodermal cells, including haematopoietic cells. OmniCytes are pluripotent (stem) cells which are CD34 positive (CD34+) and are capable of self-regeneration. These cells are further characterised by their ability to adhere to plastic (e.g. the plastic of standard tissue culture vessels) during culturing. Suitable vessels are those manufactured by Corning Incorporated, New York, USA.

OmniCytes may be further characterised by the fact that they do not require feeder layers, i.e. cells (typically inactivated by gamma irradiation which supply important metabolites without further growth or division of their own) which support the growth of the stem cells.

OmniCytes can be further characterised as obtainable by:
a) enrichment of a tissue or blood sample for $CD34^+$ cells;
b) contacting the sample with a solid support and harvesting the cells which adhere to said solid support.

Suitable tissue or blood samples include, bone marrow, peripheral blood, umbilical cord blood or tissue, placenta and samples obtained from liposuction.

More particularly, they are obtainable by:
subjecting a tissue or blood sample (preferably haemopoietic tissue such as blood or a bone marrow sample) to density gradient separation;
exposing low density cells to an affinity ligand for CD34 (preferably attached to paramagnetic beads);
recovering cells attached to said CD34 ligand;
exposing the CD34+ subpopulation to tissue culture grade plastic; and
recovering CD34+ cells adherent to the plastic.

Omnicytes are preferably adult, so non-foetal.

A sample of OmniCytes was deposited with ECACC at Porton Down, Salisbury, SP4 0JG, United Kingdom, on 24 Sep. 2004 under accession number 04092401 for the purposes of patent procedure under the Budapest Treaty. The cell line was given the name "Stem Cell OmniCyte". The deposit was made by Professor Myrtle Gordon of Willow Tree Cottage, Spinning Wheel Lane, Binfield, Berkshire RG42 5QH, Great Britain and Myrtle Gordon has authorised the applicant to refer to this deposit in this application.

One primary characterising and particularly advantageous feature of these stem cells is their ability to differentiate into a very wide variety of different cell types including ectodermal, mesodermal and endodermal cells. Thus, these stem cells can differentiate into cell types which are developmentally derived from the three germ layers of the embryo; ectoderm, mesoderm and endoderm; for example endodermal cell types such as glandular epithelial cells, mesodermal cell types such as haemopoietic and/or muscle cells, and ectodermal cell types such as nerve and/or epithelial cells.

Thus these stem cells may inter alia give rise to stomach, colon, liver, pancreas, urinary bladder, urethra, trachea, the lungs, pharynx, thyroid, parathyroid, intestine, skeletal muscle, bone, epidermis, connective tissue, heart, blood, spleen, central nervous system, lens of the eye, ganglia, nerve, pigment epidermis, hair, and mammary gland cells.

The population of OmniCytes, preferably both before and after it has been subjected to the methods of the invention, is substantially free of other cell types, in particular of cells which express CD33, CD38, HLA/DR, CD19 and CD3. Also, preferably the population is substantially free of cells dedicated to a particular lineage and/or cells carrying markers associated therewith. Preferably the population has less than 20%, more preferably less than 10%, e.g. less than 5, 4 3, 2 or 1% of lineage committed cells.

OmniCytes may be characterised as CD34+, Thy-1+, CD38−, CD33− and HLA-DR−. Preferably the cells are also AC133+, Thy-1+ and c-met+.

They are preferably a substantially homogenous population, generally uncontaminated by other stem cell subpopulations. Typically less than 5%, preferably less than 3, 2 or 1% of the cell population are not OmniCytes.

Preferably the population of cells subjected to the methods of the present invention are of mammalian origin, i.e. have been isolated from a mammalian sample or are derived from cells isolated from such a sample. Particularly preferred mammals are humans and mice. Further preferred mammals include cows, horses and companion animals.

The methods of the present invention concern culturing a population of cells. Suitable culturing conditions, for example temperature, humidity, $CO_2$, nutrients etc, as would be understood by a skilled worker. For example the cells can be cultured at about 37° C. in 5% $CO_2$/95% air.

Culture media for cells with differentiation potential are well-known in the art and any such media may be used in appropriate embodiments of the methods of the present invention. The required composition of the culture media may depend on the type of cells being cultured and the skilled man would be aware of these requirements. Thus, the skilled man would be able to determine the appropriate levels of cytokines such as leukaemia inhibitor factor (LIF) and bone morphogenetic protein (BMP), amino acids, organic substrates, micronutrients, hormones such as transferin and insulin and reducing agents such as β-mercaptoethanol to be used, as well as whether or not serum should be included in the culture medium. Commercially-available culture media are well-known and frequently used in the field. These commercially-available media may comprise all the essential components for culturing a particular cell type. Alternatively, commercially-available basic media e.g. Glasgow Minimum Essential Medium (GMEM) may be used and supplemented with any of the components discussed above. Preferably the medium is serum-free.

A further alternative culture medium which may be used is that obtained from stromal cells, such as stromal cells that can be obtained from bone marrow, fetal thymus or fetal liver. Such cells have been shown to secrete growth factors associated with stem cell maintenance. Co-culturing with such stromal cells, or in medium comprising maintenance factors supporting the proliferation of stem cells, where the stromal cells may be autologous, allogeneic or xenogeneic may be employed. Before being used in the co-culture, the mixed stromal cell preparations may be freed of haemopoietic cells employing appropriate monoclonal antibodies for removal of the undesired cells, e.g., with antibody-toxin conjugates, antibody and complement, etc. Alternatively, cloned stromal cell lines may be used where the stromal lines may be allogeneic or xenogeneic. Thus, reference above to "medium" includes cells such as stromal cells, but any reference herein to a "serum-free medium" does not include cells.

Preferably the culture media contains stem cell factor (SCF), Interleukin-3 (IL-3) or Interleukin 6 (IL-6) or a combination thereof. Optionally the media contains antibiotics such as but not limited to penicillin and streptomycin. Any combination of media components and culture conditions can be employed. Preferably however the culture media is serum free and contains SCF, IL-3, IL-6 and an antibiotic such as but not limited to penicillin and streptomycin. Optionally, said medium also contains Interleukin-1.

Optionally, the cells with differentiation potential may be cultured on a layer of feeder cells, i.e. cells which are typically inactivated by gamma irradiation and which supply important metabolites without further growth or division of their own, thereby supporting the growth of the cells with differentiation potential. As mentioned above, OmniCytes do not require feeder layers.

WO 2005/059113 discloses preferred culture media and conditions for OmniCytes and these may be used in the present methods. The media contains serum (Examples 2 and 9 of WO 2005/059113). More particularly, WO 2005/059113 discloses overlaying OmniCytes with methylcellulose containing serum and cytokines G-CSF (100 ng/ml), GM-CSF (1 ng/ml), IL-3 (5 ng/ml) and SCF (20 ng/ml). WO 2005/059113 reports that under these conditions, a heterogeneous population of cells is obtained (Example 2).

Example 9 of WO 2005/059113 explains that the Omni-Cytes divide and self-renew to form colonies of adherent stem cells, but they also give rise to adherent cells that exhibit morphologies characteristic of mesenchymal, epithelial, vascular and neural cell types. In addition, non-adherent cells are released into the methylcellulose where large colonies of haemopoietic cells form. Thus, WO 2005/059113 fails to teach a reliable method of expanding stem cells, because spontaneous differentiation takes place. This document highlights the difficulties associated with trying to expand OmniCytes, indeed these difficulties are associated with the culture of any stem cells, because cell death and/or spontaneous differentiation typically takes place. The methods of the present invention address this problem by the inclusion of an inhibitor of miRNA-181a* in the culture medium and/or by using a serum-free medium.

In the serum-free medium of the invention, Interleukin-3, Interleukin-6, SCF, and interleukin 1, if present, are each independently preferably present in a concentration of at least 10, 20, 30, 40, 50, 60, 70, 80, 90 or 100 ng/ml, more preferably at least 110, 120, 130, 140, 150, 160, 170, 180, 190, 200, 210, 220, 230 or 240 ng/ml. A concentration of about 250 ng/ml is most preferred, although about 260, 270, 280, 290, 300, 350 400, 450 or 500 may also be used. Thus, the concentration is preferably about 100-500 or 150-450, e.g. 200-

300 ng/ml, more preferably about 210-290, 220-280, 230-270 or 240-260 ng/ml. Any combination of these concentrations is contemplated, so for example, interleukin-3 may be present at about 200 ng/ml, interleukin-6 may be present at about 280 ng/ml and SCF may be present at about 250 ng/ml. Preferably, Interleukin-3, Interleukin-6 and SCF are all present at about 250 ng/ml. Interleukin-1, if present, is also preferably present at about 250 ng/ml.

Interleukin-3, Interleukin-6, SCF and Interleukin-1 are referred to herein as "growth factors". The growth factor may be recombinant, i.e. it may have been expressed from a heterologous gene in a host cell such as *E. coli* and purified therefrom. It may be isolated or purified from a non-recombinant source, which may be human or non-human.

Without wishing to be bound by theory, it appears that the success of the serum-free medium of the present invention lies in the selection of the specific combination of these factors. The use of relatively high concentrations of the factors, preferably about 250 ng/ml of each factor, is preferred.

A serum-free medium is particularly beneficial. The skilled person is aware that "serum" is a complex, undefined composition derived from animal fluids, typically blood. The term "serum" typically denotes the clear liquid that can be separated from clotted blood. As used herein "serum" also denotes undefined compositions derived from serum, e.g. compositions obtained by processing serum to remove certain components. By "serum-free" is meant that no serum or serum-derived undefined composition is present in the medium.

"Conditioned medium" is medium which has been exposed to cells and contains certain factors of unknown quality and/or quantity secreted by the cells. Thus, the serum-free medium of the invention is preferably not a conditioned medium and preferably does not include any conditioned medium as one of its components. Most preferably, the serum-free medium of the invention is "chemically defined", meaning that its chemical composition is known, i.e. no unknown ingredients are present and all ingredients are present in known amounts.

The serum-free medium of the present invention may be referred to as "unconditioned", meaning that prior to the culture method of the present invention it has not been contacted with any cells.

The serum-free media of the invention do not need to and preferably do not comprise an extracellular matrix substratum or feeder cells and culture methods involving the media preferably do not involve such a substratum or feeder cells. Thus, in preferred embodiments, an extracellular matrix substratum is not present/included. In preferred embodiments, a feeder cell not present/included. Preferably, the culture devices, e.g. flasks or dishes, which are used to culture the stem cells do not comprise and are not coated with a matrix, proteins, feeder cells and/or components derived from feeder cells.

Advantageously, the serum-free medium provided by the present invention does not require the inclusion of certain factors which are commonly used in the art for stem cell culture, but which are known or suspected to induce loss of the pluripotent state of the cells. Examples of such factors include, but are not limited to TGF-beta, epidermal growth factor (EGF), nerve growth factor (NGF), fibroblast growth factor (FGF), platelet derived growth factor (PDGF) tissue plasminogen activator, Thrombopoietin (Tpo), Flt3 (FMS-like tyrosine kinase 3), G-CSF, GM-CSF, interleukin 2, interleukin 4, interleukin 5, interleukin 7, interleukin 8, interleukin 9, interleukin 10, interleukin 11 and interferon y. In some embodiments, one or more of these factors may be present in any combination ion the serum-free media of the invention, but in preferred embodiments, one or more of these factors is not present in any significant amounts in the medium. Most preferably, none of these factors are present in any significant amounts in the medium. Thus, the serum-free medium is preferably substantially free from one or more, preferably all of the factors listed above.

By "not present in any significant amount" or "substantially free from" as used herein is meant that less than about 20, 10, 5 or 1 ng/mL, preferably less than 100, 50, 10 or 1, e.g. 0 pg/mL of the factor is present.

Certain proteins, such as albumin, insulin, insulin-like growth factor and/or transferrin may be present. These proteins may be recombinant or isolated from an animal, and they should be pure, i.e. free from contaminating proteinaceous matter.

The serum-free medium of the invention may conveniently be provided by preparing or obtaining a suitable basal medium and supplementing it with the appropriate growth factors discussed above. Preferably, the only growth factors that are added to the basal medium are Interleukin-3, Interleukin-6 and SCF, although in another embodiment, interleukin-1 is also added. A basal medium is a basic defined medium comprising salts, which is typically used as a starting point to formulate the required complex media. Basal media may also comprise further basic components such as sugars, amino acids, vitamins, buffers and the like, but basal media lack growth factors and complex nutrients. A suitable basal medium is serum-free SCGM from CellGenix (CellGenix, Am Flughafen 16, 79108 Freiburg, Germany), which contains salts, sugars, amino acids, vitamins, buffers, phenol red, 1-glutamine and beta-mercaptoethanol, as well as albumin and insulin. The skilled person will be able to select other suitable basal media, non-limiting examples of which include α-Minimum Essential Medium (α-MEM) (Gibco, UK), methylcellulose medium, Dulbecco's Modified Eagle's Medium (DMEM), StemSpan® Serum-Free Expansion Medium (SFEM), StemSpan® H3000 (both available from STEMCELL Technologies, 570 West Seventh Avenue, Suite 400, Vancouver, BC, Canada V5Z 1B3), Iscove's Modified Dulbecco's Medium (IMDM), McCoy's 5A Medium and RPMI 1640 and any variants thereof.

Thus, in another aspect there is provided a method of preparing a serum-free medium suitable for culturing stem cells, said method comprising supplementing a basal medium with Interleukin-3, Interleukin-6 and SCF. Preferably, the only growth factors that are used to supplement the basal medium are Interleukin-3, Interleukin-6 and SCF, or Interleukin-3, Interleukin-6, Interleukin-1 and SCF. Suitable concentrations of these factors are discussed above.

Suitable examples of basal media are discussed above. The method of preparing a medium of the invention may involve obtaining a basal medium, many of which are commercially available, or it may include an initial step of preparing a basal medium. The skilled person is well aware that this simply involves mixing water, preferably distilled or deionised, with appropriate minerals and salts and optionally a buffer, vitamins and the like.

The serum-free media of the invention are particularly suitable for culturing stem cells.

RNA interference (RNAi) is an important genetic regulatory mechanism that causes sequence-specific down-regulation of target RNA molecules. RNAi is mediated by "interfering RNA" (IRNA); an umbrella term which encompasses a variety of short double stranded RNA (dsRNA) molecules which function in the RNAi process, including micro-RNAs (miRNAs) and small interfering RNAs (siRNAs).

siRNAs are well-known mediators of RNAi. They are typically derived from DNA which is exogenous to the cell in which the siRNAs function. Exogenous dsRNA can be processed by the ribonuclease protein Dicer into siRNAs, which are double-stranded fragments of 19 to 25 base pairs with several unpaired bases on each 3' end forming a 3' overhang.

In contrast, micro-RNAs (miRNAs) are typically endogenous dsRNA molecules. However, once processed into mature dsRNA molecules, miRNA molecules are structurally similar to siRNAs produced from exogenous dsRNA; siRNAs (and short-hairpin RNAs (shRNAs)) resemble intermediates in the processing pathway of the endogenous miRNA genes.

Down-regulation of target genes by miRNAs and siRNAs is predominantly performed in one of two ways. Typically, siRNAs effect the down-regulation of the expression of target genes by mediating cleavage of the target messenger RNA (mRNA) molecule. A protein complex called the RNA-induced silencing complex (RISC). RISC incorporates one of the siRNA strands and uses this strand as a guide to recognize target messenger RNA molecules (mRNAs). Perfect complementarity between the siRNA guide strand and the mRNA target results in mRNA cleavage and destruction by RISC and as result of the cleavage the mRNA can no longer be translated into protein.

miRNAs, like siRNAs, use RISC to down-regulate target genes, but unlike siRNAs, most miRNAs typically do not cleave the target mRNA molecule. Instead, miRNAs preferentially target sites in the 3' untranslated regions (UTRs) of the target mRNA sequence which have imperfect complementarity to the miRNAs full length sequence. miRNAs reduce protein output through a combination of translational suppression and subsequent polyA removal and mRNA degradation.

miRNA binding sites within a target mRNA are usually located within the mRNA 3' untranslated region (3' UTR). In contrast to cleavage, translational suppression only requires base-pairing between the mRNA target and nucleotides 2 to 8 from the 5' end of the miRNAs guide strand. This region of the miRNA strand, known as the seed region, is critical for miRNA targeting and although mRNA target seed sites with imperfect seed-pairing to the seed region can be responsive, the majority of miRNA seed regions have perfect seed pairing with the target mRNA seed site.

Perfect seed complementarity does not guarantee down regulation, however. Instead, multiple factors that characterize a seed site's sequence context determine the regulatory potential of each site. More important than the characteristics of individual sites, however, is the number of seed sites within a 3' UTR. Multiple target sites within a 3' UTR give synergistic down regulation, but only if the distance between the start of the target sites is in an optimal range of about 14 to 46 nucleotides. Moreover, different dsRNAs can also cooperate and give synergistic down regulation as long as their sites are located within this optimal range. This synergistic regulation means that pairs of target sites located within an optimal distance range have a much higher regulatory potential than individual isolated sites.

It is an over-simplification to state that siRNAs and miRNAs mediate RNAi in these two discrete ways. In fact, siRNAs can function in RNAi in an miRNA-like manner, and vice versa, i.e. dsRNA molecules may function in both siRNA-like and miRNA-like down-regulation of a target mRNA transcript. This is not surprising given the above-discussed structural similarities of siRNA and miRNA molecules. Therefore, as is customary in the art and for convenience, the term "siRNA" is used herein to refer to RNA molecules which function through cleavage of target mRNA molecules, induced by base-pair binding to a coding region of an mRNA molecule. "miRNA" is used to refer to RNA molecules which through base-pair binding to short (e.g. 7 nucleotides) seed sequences within the 3'UTR of an mRNA molecule inhibit normal utilization of mRNA, thereby down regulating gene expression without the need to induce cleavage of target molecules. The terms are also used to refer to those different activities and modes of action.

Although the usual targets of siRNA and miRNA molecules are mRNA sequences, in fact any type of RNA sequence can in theory be targeted by siRNA and miRNA molecules as described above.

Functional miRNAs are processed from precursor molecules. miRNA precursors (pre-miRNA) form hairpin-loop structures, which are processed into activated linear double stranded molecules by a protein called DICER. The double-stranded miRNA molecule then gets processed by the RISC complex, leading to incorporation of one strand (the guide strand) into the RISC complex, which facilitates binding of the guide strand to a complementary sequence of the target RNA strand. Typically, miRNA molecules target mRNA molecules, i.e. the guide strand has complementarity to a region of the mRNA molecules. Binding of the miRNA guide strand to the target RNA molecule results in a combination of translational suppression and subsequent polyA removal and RNA degradation. When the target RNA is an mRNA transcript, the result is the down-regulation of the expression of the mRNA's gene.

miRNA-181a* is a naturally occurring miRNA molecule of known sequence and can be found, for instance, in miRNA databases such as those from MicroCosm Targets, microRNA.org, miRNAMAP, Applied Biosystems, TargetScan and Dharmacon.

As mentioned above, functional miRNAs are processed from precursor molecules. The precursor sequence of miRNA-181a* is set out in SEQ ID NO:1, i.e.:

5'-ugaguuuugagguugcuucagug<u>aacauucaacgcugucggugag</u>uuuggaauuaaaaucaa a<u>accaucgacgguugauuguacc</u>cuauggcuaaccaucaucuacucca-3'

Often, a single miRNA precursor molecule may be processed into a plurality of different miRNA molecules. The miRNA-181a* precursor is predominantly processed into miRNA-181a, the guide strand of which has the sequence set out in SEQ ID NO:2, i.e.:

5'-aacauucaacgcugucggugagu-3' miRNA-181a is termed the "mature" sequence as it is the miRNA which most usually results from the processing of the precursor molecule above. The miRNA-181a guide strand sequence is the first underlined sequence within the miRNA-181a precursor sequence set out above.

The second underlined sequence within the miRNA-181a precursor sequence set out above and in SEQ ID NO:1 is the miR-181a* guide strand sequence. This sequence is set out in SEQ ID NO:3, i.e.

5'-accaucgacgguugauuguacc-3' miRNA-181a* is produced from the miRNA-181 precursor molecule a minority of the time and is called the "minor" or "star" sequence.

The role of miRNA-181a* has not previously been characterized, however, as mentioned above and as shown in the Examples, the present inventors have for the first time determined that miRNA-181a* is up-regulated in cells without differentiation potential compared to cells with differentiation potential. The present inventors further identified the genetic target of miRNA-181a* and discovered that the miRNA sequence functions in the down-regulation of the expression of the sternness factor Nanog. The present inventors have further shown that inhibitors of miRNA-181a* can be effective in reversing the effects of the miRNA, i.e. in up-regulating Nanog and leading to an expansion of cells with differentiation potential.

The methods of the present invention therefore require the cells being expanded to be contacted with an inhibitor of miRNA-181a*. There are many tools known in the field which can be used to inhibit an miRNA target sequence and any such tool can be used in the present methods. Conveniently the inhibitor is a single or double stranded short RNA molecule.

Preferably, the inhibitor of miRNA-181a* is a single-stranded RNA molecule comprising a sequence which is fully or partially complementary to the miRNA-181a* guide strand sequence, i.e. to the sequence set out in SEQ ID NO:3. From hereon, for convenience, such RNA molecules will be termed "inhibitory single-stranded RNA molecules". These molecules function in a manner similar to antisense RNA, i.e. by binding to the target miRNA-181a* sequence and preventing it from being incorporated into RISC.

As used herein, the term "RNA" means a molecule comprising at least one ribonucleotide residue. By "ribonucleotide" is meant a nucleotide with a hydroxyl group at the 2' position of a beta-D-ribo-furanose moiety. The terms include double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the RNA or internally, for example at one or more nucleotides of the RNA. Nucleotides in the RNA molecules of the present invention can also comprise non-standard nucleotides, such as non-naturally occurring nucleotides or chemically synthesized nucleotides or deoxynucleotides. These altered RNAs can be referred to as analogs or analogs of naturally-occurring RNA.

Typically the inhibitory single-stranded RNA molecule comprises a sequence having at least 60%, preferably at least 75% or at least 80%, more preferably at least 85%, still more preferably at least 90%, still more preferably at least 95% complementarity to the sequence set out in SEQ ID NO:3. Alternatively or in addition, the inhibitory single-stranded RNA molecule comprises a sequence having no more than 8, preferably no more than 7, 6, 5, 4, 3, 2, or 1 base pair mismatches to the sequence set out in SEQ ID NO:3.

Most preferably the single-stranded inhibitory RNA molecule comprises a sequence which has near-perfect complementarity to the sequence set out in SEQ ID NO:3. Still more preferably, the single-stranded inhibitory RNA molecule comprises a sequence which has perfect complementarity to the sequence set out in SEQ ID NO:3, i.e. it comprises the sequence set out in SEQ ID NO:4, i.e.

5'-gguacaaucaacggucgauggu-3'

By "complementarity" and "complementary" are meant that a first nucleic acid can form hydrogen bond(s) with a second nucleic acid for example by Watson-Crick base pairing. A nucleic acid which can form hydrogen bond(s) with another nucleic acid through non-Watson-Crick base pairing also falls within the definition of having complementarity. A percent complementarity indicates the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary).

"Perfectly complementary" or "perfect complementarity" means that all sequential residues of a first nucleic acid sequence will form hydrogen bonds with the same number of sequential residues in a second nucleic acid sequence. "Near-perfect" complementary means that essentially all sequential residues of a first nucleic acid sequence will form hydrogen bonds with the same number of sequential residues in a second nucleic acid sequence, however, due to the fact that the first nucleic acid is prepared by an imperfect process such as transcription or a molecular biological process involving the use of biological molecules, the first sequence may not be 100% complementary to the second sequence. Typically, "near-perfect complementarity" means that a first nucleic acid sequence has at least 95% complementarity with a second nucleic acid sequence and/or no more than 2 base pair mismatches with the second nucleic acid sequence.

By "inhibition" or "down-regulation" of a gene is meant a reduction of the level of expression of a gene(s), or levels of the polypeptide(s) encoded by a gene or the activity thereof, or levels of the RNA molecule(s) transcribed from a gene below that observed in the absence of the inhibitors used in the methods of the present invention. If an RNA molecule is said to be "down-regulated" this means that the level, activity or biological availability of the RNA molecule is reduced below that observed in the absence of the inhibitor.

By "activation" or "up-regulation" of a gene is meant an increase in the level of expression of a gene(s), or levels of the polypeptide(s) encoded by a gene or the activity thereof, or levels of the RNA molecule(s) transcribed from a gene above that observed in the absence of the inhibitors used in the methods of the present invention.

The inhibitors of the present invention down-regulate miRNA-181a*, i.e. they result in a reduction in the levels, activity or biological availability of this miRNA in the cells contacted therewith. As shown in the Examples, since miRNA-181a* itself down-regulates Nanog via interaction with the 3'-UTR of the Nanog mRNA transcript, use of the miRNA-181a* inhibitors of the present invention result in the up-regulation of the Nanog gene.

Provided that the single-stranded inhibitory RNA molecule comprises a sequence with sufficient complementarity to down-regulate the miRNA-181a* guide strand sequence, the RNA molecule can be of any length. The skilled man would be aware of the length limitations of such molecules, for instance in relation to the ability of the molecule to enter the cells. Optionally, the single-stranded inhibitory RNA molecule is from 8 to 80 nucleotides in length, preferably 12 to 50 nucleotides in length, more preferably 15 to 30 nucleotides in length, most preferably 22 nucleotides in length.

Alternatively, the inhibitor of miRNA-181a* is itself a short double-stranded RNA molecule such as an siRNA or miRNA molecule, which is capable of down-regulating miRNA-181a*.

The term "small interfering RNA" or "siRNA" as used herein refers to an RNA molecule which mediates sequence-specific-mediated cleavage of one or more target RNA molecules. siRNAs and miRNAs typically contain one strand (the guide strand) comprising a sequence with sufficient complementarity to a region of a target RNA transcript, in this case the miRNA-181a* guide strand transcript, i.e. the sequence set out in SEQ ID NO:3, to result in down-regulation of said target transcript.

Preferably the short double-stranded RNA (dsRNA) molecules used in the methods of the present invention comprise a strand which comprises a sequence having at least 60%, preferably at least 75% or at least 80%, more preferably at least 85%, still more preferably at least 90%, still more preferably at least 95% complementarity to the sequence set out in SEQ ID NO:3. Alternatively or in addition, the inhibitory short double-stranded RNA (dsRNA) molecules comprise a strand comprising a sequence having no more than 8, preferably no more than 7, 6, 5, 4, 3, 2, or 1 mismatches to the sequence set out in SEQ ID NO:3.

More preferably the short double-stranded RNA (dsRNA) molecules used in the methods of the present invention comprise a strand which comprises a sequence having near-perfect complementarity to the sequence set out in SEQ ID NO:3. Still more preferably the short double-stranded RNA (dsRNA) molecules used in the methods of the present invention comprise a strand which comprises a sequence having perfect complementarity to the sequence set out in SEQ ID NO:3, i.e. comprising the sequence set out in SEQ ID NO:4, i.e.

5'-gguacaaucaacggucgauggu-3'

Sequence alignments, percent complementarity and percent identity calculations may be determined using any method or tool known in the art including but not limited to the Megalign program of the LASARGENE bioinformatics computing suite (DNASTAR Inc., Madison, Wis.), the Clustal V method of alignment (Higgins and Sharp (1989) CABIOS. 5:151-153), RNAhybrid (http://www.ncbi.nlm.nih.gov/pubmed/15383676; http://bibiserv.techfak.uni-bielefeld.de/mahybrid/), Clustal W2 (http://www.ebi.ac.uk/Tools/clustalw2/index.html), BLAST (http://blast.ncbi.nlm.nih.gov/) and EMBOSS Pairwise Alignment Algorithms (http://www.ebi.ac.uk/Tools/emboss/align/index.html), the latter of which includes the Needleman-Wunsch algorithm for global alignment (http://emboss.sourceforge.net/apps/cvs/emboss/apps/needle.html) and the Smith-Waterman algorithm for local alignment (http://emboss.sourceforge.net/apps/cvs/emboss/apps/water.html). Preferably RNAhybrid (http://www.ncbi.nlm.nih.qov/pubmed/15383676; http://bibiserv.techfak.uni-bielefeld.de/mahybrid/) is used. The skilled man will be able to set the parameters of these tools to suit his desired purpose.

Preferably each strand of the short dsRNA duplex is at least 16, more preferably at least 19 nucleotides in length. Preferably the duplex is hybridised over a length of at least 12, more preferably at least 15, more preferably 17, still more preferably at least 19 nucleotides. Each strand may be exactly 19 nucleotides in length or in a preferred embodiment one strand is 25 nucleotides and the other 27 nucleotides in length. Preferably the duplex length is less than 30 nucleotides since duplexes exceeding this length may have an increased risk of inducing the interferon response. The strands forming the dsRNA duplex may be of equal or unequal lengths.

Most preferably the short dsRNA molecule is a short interfering RNA (siRNA) molecule. Preferably the short dsRNA molecule used in the above methods is from 16 nucleotides to 30 nucleotides in length, more preferably 19 to 30 nucleotides in length, still more preferably 19 to 23 nucleotides in length, most preferably 21 nucleotides in length.

Optionally the short dsRNA molecules consist of the two strands stably base-paired together with a number of unpaired nucleotides at the 3' end of each strand forming 3' overhangs. The number of unpaired nucleotides forming the 3' overhang of each strand is preferably in the range of 1 to 5 nucleotides, more preferably 1 to 3 nucleotides and most preferably 2 nucleotides.

Various tools for the design and analysis of single and double-stranded RNA molecules are well-known, which permit one of ordinary skill in the art to determine those RNA molecules which can achieve effective and specific down-regulation of a target RNA transcript. Established methods include, for example, the GPboost and Reynolds algorithms (PMIDs: 15201190, 14758366). In addition, the ability of a short dsRNA to cause effective down-regulation of a target RNA can be evaluated using standard techniques for measuring the levels of RNA or protein in cells. For example, an inhibitory single-stranded or double-stranded RNA of the invention can be delivered to cultured cells, and the levels of target RNA (miRNA-181a*) can be measured by techniques including but not limited to Northern blot or dot blotting techniques, or by quantitative RT-PCR.

Preferably the inhibitory RNAs possess none of the motifs aaaa, cccc, gggg, or tttt. Preferably the inhibitory RNAs have a GC-percentage of at least 20% and no more than 75%, i.e. between 20% and 75%, preferably between 20% and 55%. The short dsRNAs of the above methods are ideally thermodynamically stable duplexes, in which case the GC percentage of each strand is at least 25% and no more than 75%, i.e. between 25% and 75%, preferably between 30% and 55%.

Tools and algorithms for determining whether or not RNAs possess the motifs aaaa, cccc, gggg or tttt and for determining the percentage GC content of the molecules/strands are well known to the skilled artisan. Such tools include those described and referenced in Saetrom and Snove, (2004) *Biochem Biophys Res Commun* 321: 247-253 and Vert et al., (2006) *BMC Bioinformatics* 7: 520 (17 pages).

Short dsRNAs can induce down-regulation of non-target transcripts that have a limited number of mismatches to the RNA strand which is incorporated into the RISC protein complex. This reduces the efficiency of the short dsRNA molecule and is therefore not desired. Consequently, short dsRNA molecules should have limited complementarity to transcripts other than the intended target to prevent unintended off-target effects. The probability of a short dsRNA candidate having cleavage-based off-target effects is a function of its complementarity to non-target RNA sequences and can be determined by any known method in the art. Optionally, an ungapped Smith-Waterman method (T F Smith & M S Waterman (1981) *Journal of molecular biology* 147: 195-197) can be used to screen the candidate short dsRNA against the Ensembl (Flicek, P., et al. (2008) Ensembl 2008. *Nucleic Acids Res* 36: D 707-714) human transcriptome database (Snøve, O., Jr., et al. (2004) *Biochem Biophys Res Commun* 325: 769-773) to identify a short dsRNA's potential off-target transcripts. Alternatively, the short dsRNA can be screened against a population of chosen RNA sequences, for example a selection of GenBank sequences, which do not encompass the entire Ensembl human transcriptome database. Alternatively a Hamming distance measure can be used.

Preferably, the short dsRNA molecules have more than two mismatches to the identified off-target transcripts Alternatively viewed, preferably the short dsRNA molecules have a Hamming distance of 2 or greater to all potential off-target transcripts.

Optionally, the short dsRNA molecules have characteristics in common with known highly effective standard siRNAs. Preferably, one or both strands of the short dsRNA has a GPboost score of more than 0.1. GPboost is a known genetic programming-based prediction system of siRNA efficacy and the methods used for determining the GPboost score of siRNA strands is disclosed in "Predicting the efficacy of short oligonucleotides in antisense and RNAi experiments with boosted genetic programming", Pål Saetrom (2004) *Bioinformatics* 20(17): 3055-3063, the content of which is incorporated here by reference. Alternatively or in addition, the short dsRNA molecules possess specific sequence features which are associated with highly effective siRNAs. The algorithm described by Reynolds [Reynolds et al. (2004) *Nature biotechnology* 22(3):326-330], which is incorporated here by reference permits the determination of whether or not short dsRNAs possess sufficient features of this type. One of ordinary skill in the art would be able to define and refine his threshold for his particular purpose.

Optionally, the short dsRNA molecules contain position-specific sequence motifs which are associated with highly effective siRNAs. siRNA efficacy prediction algorithms are well-known in the art and motifs which are associated with highly-effective siRNAs are discussed in Saetrom and Snove, (2004) *Biochem Biophys Res Commun* 321: 247-253, the content of which is incorporated here by reference.

Preferably the short dsRNA molecule is capable of direct entry into the RNAi machinery of a cell or is capable of being processed by Dicer before entry into the RNAi machinery of a cell. Methods of determining whether or not a short dsRNA molecule is capable of being processed by Dicer before entry into the RNAi machinery of a cell are well-known in the art, for instance in vitro Dicer assays such as that disclosed in Tiemann et al. (2010) *RNA* 16(6): 1275-1284 and Rose et al. (2005) *Nucleic Acid Research* 33(13):4140-4156.

As mentioned above, typically only the guide strand of a short dsRNA molecule is capable of effectively and specifically down-regulating the target RNA transcript (miRNA-181a*). Therefore, preferably that strand is preferentially loaded into RISC. The design of double-stranded RNA molecules in which one strand is preferentially loaded into RISC is within the competence of one of ordinary skill in the art. For instance, the 5' end of the strand of the short dsRNA molecule which targets the target RNA transcript can be made or selected to be less thermodynamically stable than the 5' end of the other strand. Preferably there is a large difference in duplex thermodynamic end stability such that the 5' end of the strand of the short dsRNA molecule which targets the target RNA transcript is less thermodynamically stable than the 5' end of the other strand. The absolute value of the difference in duplex thermodynamic end stability ($\Delta\Delta G$) can be calculated in accordance with any method standard in the art. Optionally, the absolute value of the difference in duplex thermodynamic end stability is calculated by RNAfold (Hofacker et al., (2003) *Nucleic Acids Research* Vol. 31, No. 13, pp 3429-3431) by considering the 5 closing nucleotides at the ends of the duplex. Preferably the absolute value of the difference in duplex thermodynamic end stability as calculated by RNAfold is more than 0 kcal/mol, more preferably more than 1 kcal/mol, more preferably more than 3 kcal/mol.

Many standard tools for short dsRNA design, such as those described above, provide means for assessing this property of the molecules. For instance, double-stranded molecules can be selected if they have thermodynamic properties which favour the incorporation of one strand over the other into the RNAi machinery. Alternatively, the preferential loading of one strand can be achieved by using dsRNAs which contain RNA that differs from naturally-occurring RNA by the addition, deletion, substitution and/or alteration of one or more nucleotides. Such modifications are well-known to the skilled man and are discussed further below.

Dicer is a ribonuclease protein which cleaves exogenous dsRNA into double-stranded fragments of 19 to 25 base pairs with several unpaired bases on each 3' end forming a 3' overhang. The short dsRNAs used in the above-methods may be Dicer-substrate siRNAs (D-siRNAs). siRNAs designed as Dicer substrates can have increased potency compared to standard length siRNAs and shRNAs.

D-siRNAs are asymmetric siRNA-duplexes in which the strands are between 22 and 30 nucleotides in length. Typically, one strand (the passenger strand) is 22 to 28 nucleotides long, preferably 25 nucleotides long, and the other strand (the guide strand) is 24 to 30 nucleotides long, preferably 27 nucleotides long, such that the duplex at the 3' end of the passenger strand is blunt-ended and the duplex has an overhang on the 3' end of the guide strand. The overhang is 1 to 3 nucleotides in length, preferably 2 nucleotides. The passenger strand may also contain a 5' phosphate.

Typically in D-siRNAs, the two nucleotides at the 3' end of the passenger strand are deoxyribonucleic acids (DNAs) rather than ribonucleic acids (RNAs). The DNAs and the blunt-ended duplex ensure that the enzyme Dicer processes the duplex into a 21mer duplex consisting of the 21 nucleotides at the 5' and 3' ends of the original D-siRNA's passenger and guide strands respectively.

Methods of extending standard 19mer siRNA molecules into D-siRNAs are well-known in the art, for instance as described in Hefner et al. (2008) *J. Biomol. Tech.* 19(4):231-237.

When extended to 27mer/25mer D-siRNAs, many siRNA molecules have an end structure where the predicted number of unpaired bases at the 3' end of the passenger strand is less than or equal to the predicted number of unpaired bases at the 5' end of the guide strand. Based on the structure of known miRNAs and the binding requirements of the Dicer PAZ-domain, this structure is most likely suboptimal for Dicer processing and so, while useful as siRNA molecules, such duplexes are less useful when extended to Dicer-substrate siRNA molecules. Therefore, preferably the short dsRNAs used in the methods of the present invention do not possess such a structure and rather the predicted number of unpaired bases at the 3' end of the passenger strand is greater than the predicted number of unpaired bases at the 5' end of the guide strand.

Optionally the inhibitory RNA molecules used in the above methods can comprise modifications, i.e. RNA that differs from naturally-occurring RNA by the addition, deletion, substitution and/or alteration of one or more nucleotides. For instance, the two strands of a dsRNA molecule may be linked by a linking component such as a chemical linking group or an oligonucleotide linker with the result that the resulting structure of the dsRNA is a hairpin structure. The linking component must not block or otherwise negatively affect the activity of the dsRNA, for instance by blocking loading of strands into the RISC complex or association with Dicer. Many suitable chemical linking groups are known in the art. If an oligonucleotide linker is used, it may be of any sequence or length provided that full functionality of the dsRNA is retained. Preferably, the linker sequence contains higher amounts of uridines and guanines than other nucleotide bases and has a preferred length of about 4 to 9, more preferably 8 or 9 residues.

Modifications can be included in the short dsRNA, provided that the modification does not prevent the RNA composition from serving as a substrate for Dicer. One or more modifications can be made that enhance Dicer processing of the dsRNA, that result in more effective RNAi generation, that support a greater RNAi effect, that result in greater potency per each dsRNA molecule to be delivered to the cell.

Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the RNA. Where multiple modifications are present, they may be the same or different. Modifications to bases, sugar moieties, the phosphate backbone, and their combinations are contemplated. In dsRNA molecules, either 5'-terminus can be phosphorylated.

Short dsRNA molecules can be modified for Dicer processing by suitable modifiers located at the 3' end of the passenger strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). Deoxynucleotides can be used as the modifiers. When nucleotide modifiers are utilized, 1-3 nucleotide modifiers, or 2 nucleotide modifiers are substituted for the ribonucleotides on the 3' end of the passenger strand. When sterically hindered molecules are utilized, they are attached to the ribonucleotide at the 3' end of the passenger strand. Thus, the length of the strand does not change with the incorporation of the modifiers. Optionally two DNA bases are substituted in the dsRNA to direct the orientation of Dicer processing. Optionally, two terminal DNA bases are located on the 3' end of the passenger strand in place of two ribonucleotides forming a blunt end of the duplex on the 5' end of the guide strand and the 3' end of the passenger strand, and a two-nucleotide RNA overhang is located on the 3'-end of the guide strand. This is an asymmetric composition with DNA on the blunt end and RNA bases on the overhanging end.

Examples of modifications contemplated for the phosphate backbone of inhibitory RNA molecules include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNAs, could also be incorporated. Many other modifications are known and can be used so long as the above criteria are satisfied.

The inhibitory RNAs used in the methods of the present invention can also comprise partially purified RNA, substantially pure RNA, synthetic RNA, or recombinantly produced RNA. Other possible alterations to the RNAs include addition of non-nucleotide material to the end(s) of the RNA or to one or more internal nucleotides of the NA; modifications that make the RNA resistant to nuclease digestion (e.g., the use of 2'-substituted ribonucleotides or modifications to the sugar-phosphate backbone); or the substitution of one or more nucleotides in the RNA with deoxyribonucleotides.

In the above methods, the population of cells is contacted with an inhibitor which is preferably an RNA molecule. The RNA molecule can be administered to said cells by using any suitable delivery reagents in conjunction with the RNA. Such suitable delivery reagents include the Mirus Transit TKO lipophilic reagent; lipofectin; lipofectamine; cellfectin; or polycations (e.g., polylysine), virus-based particles, electroporation or liposomes. A preferred delivery reagent is a liposome. A variety of methods are known for preparing liposomes, for example as described in Szoka et al. (1980), Ann. Rev. Biophys. Bioeng. 9: 467; and U.S. Pat. Nos. 4,235,871 and 5,019,369, the entire disclosures of which are herein incorporated by reference.

Particularly preferably, the liposomes encapsulating RNAs are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Recombinant plasmids which express RNAs can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express RNA and methods for delivering such vectors to a cell are known within the art.

The single or double-stranded RNAs may be provided alone or in combination with other active agent(s) known to have an effect in the particular method being considered. The other active agent(s) may be administered simultaneously, separately or sequentially with the RNAs disclosed above. Thus, it is possible to use a single RNA, a combination of two or more RNAs or, if applicable, a combination of said RNA(s) and other active substance(s).

The single and double stranded RNA molecules discussed above can be produced by any suitable method, for example synthetically or by expression in cells using standard molecular biology techniques which are well-known to the skilled artisan. For example, the RNAs can be chemically synthesized or recombinantly produced using methods known in the art, such as the *Drosophila* in vitro system described in U.S. published application 2002/0086356 of Tuschl et al., or the methods of synthesizing RNA molecules described in Verma and Eckstein (1998) *Annu Rev Biochem* 67: 99-134, the entire disclosures of which are herein incorporated by reference. The RNAs may be chemically synthesized using appropriately protected ribonucleoside phosphoramidites and a conventional DNA/RNA synthesizer. Double-stranded RNAs can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

The RNAs can also be expressed from recombinant circular or linear DNA plasmids using any suitable promoter. Suitable promoters for expressing short RNAs from a plasmid include, for example, the U6 or H1 RNA pol III promoter sequences and the cytomegalovirus promoter. Selection of other suitable promoters is within the skill in the art. The recombinant plasmids can also comprise inducible or regulatable promoters for expression of the RNA in a particular tissue or in a particular intracellular environment.

The RNAs expressed from recombinant plasmids can be isolated from cultured cell expression systems by standard techniques. The double stranded short RNAs discussed above can be expressed from a recombinant plasmid either as two separate, complementary RNA molecules, or as a single RNA molecule with two complementary regions.

Selection of plasmids suitable for expressing RNAs, methods for inserting nucleic acid sequences for expressing the RNAs into the plasmid, and methods of delivering the recombinant plasmid to the cells of interest are within the skill in the art. See, for example Tuschl, T. (2002), Nat. Biotechnol. 20: 446-448 and Brummelkamp T R et al. (2002), Science 296: 550-553, the entire disclosures of which are herein incorporated by reference.

The RNAs can also be expressed from recombinant viral vectors intracellularly in vivo. The recombinant viral vectors of the invention comprise sequences encoding the RNAs and any suitable promoter for expressing the RNA sequences. Suitable promoters include, for example, the U6 or H1 RNA pol III promoter sequences and the cytomegalovirus promoter. Selection of other suitable promoters is within the skill in the art. The double stranded short RNAs discussed above can be expressed from a recombinant viral vector either as two separate, complementary RNA molecules, or as a single RNA molecule with two complementary regions. Any viral vector capable of accepting the coding sequences for the RNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

Selection of recombinant viral vectors suitable for use in the invention, methods for inserting nucleic acid sequences for expressing the RNA into the vector, and methods of delivering the viral vector to the cells of interest are within the skill in the art. See, for example, Dornburg R (1995), Gene Therap. 2: 301-310, the entire disclosure of which is herein incorporated by reference.

Preferably an inhibitor of STAT3 is also included in the culture medium, i.e. preferably the methods above also comprise contacting said cells with an inhibitor of STAT3. STAT3 (signal transducer and activator of transcription 3) is a transcription factor which in humans is encoded by the STAT3 gene. Constitutive STAT3 activation is associated with various human cancers. The gene has anti-apoptotic as well as proliferative effects. Preferably the inhibitor of STAT3 is a single-stranded RNA molecule comprising a sequence having sufficient complementarity to a sequence within the STAT3 mRNA sequence to cause down-regulation thereof. Alternatively the inhibitor is a short double-stranded RNA molecule, such as an siRNA molecule, at least one strand of which has sufficient complementarity to a sequence within the STAT3 mRNA sequence to cause down-regulation thereof. The discussion anywhere above of complementarity, single and double-stranded inhibitory molecules, siRNA molecules and down-regulation applies equally to the STAT3 inhibitors disclosed here. Optionally, the inhibitor of STAT3 is WP1066. The skilled man would be able to determine the appropriate levels of STAT3 inhibitors to be used. If WP1066 is used then preferably it is used at a concentration of 2 to 20 ng/ml, more preferably 5 to 15 ng/ml, most preferably about 10 ng/ml.

In a further aspect the present invention provides a method of screening for a compound which maintains the differentiation potential of a population of cells with differentiation potential, said method comprising culturing said cells in the presence of a test compound and subsequently determining either;

i) the level of miRNA-181a* present in said cells, wherein a reduced level of miRNA-181a* compared to the level of miRNA-181a* present in a control population of said cells cultured in the absence of said test compound is indicative of said test compound maintaining the differentiation potential of said population of cells; or ii) the level of Nanog expression in said cells, wherein an increased level of Nanog expression compared to the level of Nanog expression observed in a control population of said cells cultured in the absence of said test compound is indicative of said test compound maintaining the differentiation potential of said population of cells.

The levels of miRNA in a population of cells can be determined by any method known in the art, for instance by techniques including but not limited to Northern blot or dot blotting techniques, or by quantitative RT-PCR.

The level of Nanog expression in a population of cells can be determined by any method of determining protein level expression or activity known in the art. For instance by Western blotting flow cytometry or immunofluorescence.

The cell types, culture conditions and media and definitions discussed above in relation to the methods of culturing a population of cells with differentiation potential and of maintaining the differentiation potential of a population of cells with differentiation potential apply equally to this method of screening for a compound which maintains the differentiation potential of a population of cells with differentiation potential.

Discussed herein are "mimics" of miRNA-181a*. Such a molecule is optionally a single-stranded RNA molecule comprising a sequence which has identity to the miRNA-181a* guide strand sequence, i.e. to the sequence set out in SEQ ID NO:3. Preferably, however, the miRNA-181a* mimic is a double-stranded molecule, one strand of which has identity to the miRNA-181a* guide strand sequence, i.e. to the sequence set out in SEQ ID NO:3.

Preferably the single- or double-stranded mimic comprises a sequence having at least 60%, preferably at least 75% or at least 80%, more preferably at least 85%, still more preferably at least 90%, still more preferably at least 95% identity to the sequence set out in SEQ ID NO:3. Alternatively or in addition, the mimic comprises a sequence having no more than 8, preferably no more than 7, 6, 5, 4, 3, 2, or 1 nucleotides which are non-identical with the sequence set out in SEQ ID NO:3.

Most preferably the miRNA-181a* mimic comprises a sequence which has near-perfect identity to the sequence set out in SEQ ID NO:3. Still more preferably, the miRNA-181a* mimic comprises a sequence which has perfect identity to the sequence set out in SEQ ID NO:3.

By "identity", "identical" or "sequence identity" is meant that a first nucleic acid is identical in sequence to a second nucleic acid sequence. A percent identity indicates the percentage of residues in a first nucleic acid molecule that are identical to a second nucleic acid sequence (e.g., 5, 6, 7, 8, 9, 10 out of 10 being 50%, 60%, 70%, 80%, 90%, and 100% identical).

"Perfect identity" or "perfectly identical" means that all sequential residues of a first nucleic acid sequence are identical to the same number of sequential residues in a second nucleic acid sequence. "Near-perfect" identity means that essentially all sequential residues of a first nucleic acid sequence are identical to the same number of sequential residues in a second nucleic acid sequence, however, due to the fact that the first nucleic acid is prepared by an imperfect process such as transcription or a molecular biological process involving the use of biological molecules, the first sequence may not be 100% identical to the second sequence. Typically, "near-perfect identity" means that a first nucleic acid sequence has at least 95% identity and/or no more than 2 nucleotides which are non-identical with the second nucleic acid sequence.

In a further aspect the present invention provides a method of culturing a population of cells with differentiation potential, said method comprising contacting said cells with a mimic of miRNA-21.

Alternatively viewed, the present invention further provides a method of maintaining the differentiation potential of a population of cells with differentiation potential, said method comprising contacting said cell cells with a mimic of miRNA-21.

miRNA-21 is a naturally occurring miRNA molecule of known sequence and can be found, for instance, in miRNA databases such as those from MicroCosm Targets, microRNA.org, miRNAMAP, Applied Biosystems, TargetScan and Dharmacon.

The guide strand of miRNA-21 has the sequence set out in SEQ ID NO:5, i.e.

5'-uagcuuaucagacugauguuga-3'

The miRNA-21 mimic is optionally a single-stranded RNA molecule comprising a sequence which has identity to the miRNA-21 guide strand sequence, i.e. to the sequence set out in SEQ ID NO:5. Preferably, however, the miRNA-21 mimic is a double-stranded molecule, one strand of which has identity to the miRNA-21 guide strand sequence, i.e. to the sequence set out in SEQ ID NO:5.

Preferably the single- or double-stranded mimic comprises a sequence having at least 60%, preferably at least 75% or at least 80%, more preferably at least 85%, still more preferably at least 90%, still more preferably at least 95% identity to the sequence set out in SEQ ID NO:5. Alternatively or in addition, the mimic comprises a sequence having no more than 8, preferably no more than 7, 6, 5, 4, 3, 2, or 1 nucleotides which are non-identical with the sequence set out in SEQ ID NO:5.

Most preferably the miRNA-21 mimic comprises a sequence which has near-perfect identity to the sequence set out in SEQ ID NO:5. Still more preferably, the miRNA-21 mimic comprises a sequence which has perfect identity to the sequence set out in SEQ ID NO:5.

The cell types, culture conditions, media, other preferred embodiments and definitions discussed anywhere above in relation to the first aspect of the invention apply equally to this further aspect of the present invention.

In particular, by "identity", "identical" or "sequence identity" is meant that a first nucleic acid is identical in sequence to a second nucleic acid sequence. A percent identity indicates the percentage of residues in a first nucleic acid molecule that are identical to a second nucleic acid sequence (e.g., 5, 6, 7, 8, 9, 10 out of 10 being 50%, 60%, 70%, 80%, 90%, and 100% identical).

"Perfect identity" or "perfectly identical" means that all sequential residues of a first nucleic acid sequence are identical to the same number of sequential residues in a second nucleic acid sequence. "Near-perfect" identity means that essentially all sequential residues of a first nucleic acid sequence are identical to the same number of sequential residues in a second nucleic acid sequence, however, due to the fact that the first nucleic acid is prepared by an imperfect process such as transcription or a molecular biological process involving the use of biological molecules, the first sequence may not be 100% identical to the second sequence. Typically, "near-perfect identity" means that a first nucleic acid sequence has at least 95% identity and/or no more than 2 nucleotides which are non-identical with the second nucleic acid sequence.

Discussed herein are "inhibitors of miRNA-21". There are many tools known in the field which can be used to inhibit an miRNA sequence and any such toll is considered here. Preferably, the inhibitor of miRNA-21 is a single-stranded RNA molecule comprising a sequence which is fully or partially complementary to the miRNA-21 guide strand sequence, i.e. to the sequence set out in SEQ ID NO:5.

Typically the inhibitory single-stranded RNA molecule comprises a sequence having at least 60%, preferably at least 75% or at least 80%, more preferably at least 85%, still more preferably at least 90%, still more preferably at least 95% complementarity to the sequence set out in SEQ ID NO:5. Alternatively or in addition, the inhibitory single-stranded RNA molecule comprises a sequence having no more than 8, preferably no more than 7, 6, 5, 4, 3, 2, or 1 base pair mismatches to the sequence set out in SEQ ID NO:5.

Most preferably the single-stranded inhibitory RNA molecule comprises a sequence which has near-perfect complementarity to the sequence set out in SEQ ID NO:5. Still more preferably, the single-stranded inhibitory RNA molecule comprises a sequence which has perfect complementarity to the sequence set out in SEQ ID NO:5, i.e. it comprises the sequence set out in SEQ ID NO:6, i.e.

5'-ucaacaucagucugauaagcua-3'

Alternatively, the inhibitor of miRNA-21 is itself a short double-stranded RNA molecule such as an siRNA or miRNA molecule, which is capable of down-regulating miRNA-21. siRNAs and miRNAs typically contain one strand (the guide strand) comprising a sequence with sufficient complementarity to a region of a target RNA transcript, in this case the miRNA-21 guide strand transcript, i.e. the sequence set out in SEQ ID NO:5, to result in down-regulation of said target transcript.

Preferably the short double-stranded RNA (dsRNA) molecules comprise a strand which comprises a sequence having at least 60%, preferably at least 75% or at least 80%, more preferably at least 85%, still more preferably at least 90%, still more preferably at least 95% complementarity to the sequence set out in SEQ ID NO:5. Alternatively or in addition, the inhibitory short double-stranded RNA (dsRNA) molecules comprise a strand comprising a sequence having no more than 8, preferably no more than 7, 6, 5, 4, 3, 2, or 1 mismatches to the sequence set out in SEQ ID NO:5.

More preferably the short double-stranded RNA (dsRNA) molecules comprise a strand which comprises a sequence having near-perfect complementarity to the sequence set out in SEQ ID NO:5. Still more preferably the short double-stranded RNA (dsRNA) molecules comprise a strand which comprises a sequence having perfect complementarity to the sequence set out in SEQ ID NO:5, i.e. comprising the sequence set out in SEQ ID NO:6, i.e.

5'-ucaacaucagucugauaagcua-3'

The inventors have also found that when the starting population is OmniCytes, then during the initial stages of the culture in serum-free medium the cells retain all or substantially all of the characteristics of the starting cell population, so the method allows the survival and proliferation of Omni-Cytes, particularly for up to 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 or 72 h, e.g. 1-3 days. Surprisingly, the inventors found that during the culture of OmniCytes in the serum-free media of the invention, the cell population undergoes some changes and gradually becomes predominantly or entirely non-adherent, and at least a proportion of cells ceases to express CD34, so the population becomes $CD34^{low}$, or CD34 negative, but the pluripotent state of the cells is maintained and spontaneous differentiation is avoided.

By "$CD34^{low}$" is meant that less than 50% of the members of the cell population express CD34, preferably less than 45, 40, or 35%.

This stem cell population arising from culture of Omni-Cytes with serum-free medium of the invention may conveniently be referred to as "progeny stem cells", or more particularly "OmniCyte progeny stem cells".

A representative sample of OmniCyte progeny stem cells was deposited with the NIBSC/UK Stem Cell Bank (Blanche Lane, Potters Bar, Hertfordshire EN6 3QG, United Kingdom) by Professor Nagy Habib of Department of Surgery, Imperial College London, Hammersmith Hospital, Du Cane Road, London W12 0NN, UK. Accession number P-10-011 was allocated to this deposit on 10 Dec. 2010. Nagy Habib has authorised the applicant to refer to this deposit in this application, and he has given his unreserved and irrevocable consent for the deposited material to be made available to the public in accordance with Rule 33 of the European Patent Convention (EPC).

The term "progeny" is used herein to indicate that the stem cells are derived from a starting population from which the progeny stem cells differ in at least one characteristic. Preferably, this characteristic is the ability to adhere to plastic and/or the level of CD34 expression. Preferably, the progeny cells retain the pluripotent characteristics of the starting population, and most preferably they are capable of differentiating into mesodermal, endodermal and ectodermal cell types.

As set out above, OmniCytes are capable of adhering to tissue-culture grade plastic, so they may conveniently be called "adherent", whereas OmniCyte progeny stem cells are "non-adherent". Adherence may be assayed by incubating the cells in tissue culture plastic vessels for at least 2 hours, preferably at least 3 hours e.g. 3-5 hours and subsequently washing the vessels with a buffer such as HBSS (Hanks balanced salt solution). Cells are "adherent" if they can withstand at least 3 vigorous washes, whereas those cells which are washed off the vessel during such washing steps are "non-adherent".

Thus, in another aspect the present invention provides a method of generating a population of progeny stem cells. The method comprises contacting a starting population of stem cells with serum-free medium of the invention, and optionally contacting the starting population of cells with an inhibitor of miRNA181a*, and incubating the cell population for a suitable length of time, wherein a population of progeny stem cells is generated. Optionally, the method further comprises harvesting the progeny stem cell population. Preferably, the starting population of stem cells is OmniCytes and the method yields a population of OmniCyte progeny stem cells. Suitable culture conditions are discussed elsewhere herein.

Any of the methods of the invention preferably employ OmniCytes as the starting population. OmniCytes may be obtained by known methods as discussed above. In an embodiment, the methods of the invention comprise a preliminary step of selecting OmniCytes by selecting stem cells which are CD34+ and capable of adhering to a solid support. In such an embodiment the method preferably comprises subjecting a suitable in vitro sample, e.g. a bone marrow or blood sample, to a procedure which enriches for those cells which are $CD34^+$ and capable of adhering to a solid support.

In an embodiment, the method comprises
a) enrichment of tissue or blood sample for $CD34^+$ cells;
b) contacting the sample with a solid support and harvesting the cells which adhere to said solid support; and
c) culturing the harvested cells in serum-free medium.

Suitable tissue or blood samples include bone marrow, peripheral blood, umbilical cord blood or tissue, placenta and samples obtained from liposuction.

Steps a) and b) may be performed in either order, but step c) is the final step of the method. Preferably step b) is performed on the product of step (a) and thus reference to 'the sample' in step b) includes reference to a bone marrow, peripheral blood, umbilical cord blood, umbilical tissue, placenta or liposuction sample or a fraction of such a sample which has already been subjected to an enrichment or other step, typically to select $CD34^+$ cells. The culture in serum-free medium is carried out in accordance with the media and methods disclosed herein.

In one embodiment, the method comprises
(i) subjecting a tissue or blood sample, preferably haemopoietic tissue such as blood or a bone marrow sample, to density gradient separation;
(ii) exposing low density cells to an affinity ligand for CD34 (preferably attached to paramagnetic beads);
(iii) recovering cells attached to said CD34 ligand;
(iv) exposing the $CD34^+$ subpopulation to tissue culture grade plastic;
(v) recovering $CD34^+$ cells adherent to the plastic; and
(vi) culturing said cells in serum-free medium.
The culture in serum-free medium is carried out in accordance with the media and methods disclosed herein. Prior or during said culture, the cells may be contacted with an inhibitor of miRNA181a*.

Blood samples are preferably obtained following stem cell mobilisation with G-CSF to increase the numbers of stem cells in the circulation. For example, 5 µg/kg body weight/day may be administered subcutaneously for 5 days. It is also possible to obtain direct bone marrow samples, e.g. through aspiration. However, the use of in vitro samples is preferred, so the methods of the invention preferably do not involve a step of collecting the sample. Umbilical cord and placenta samples are especially preferred.

The tissue or blood in vitro sample may be processed to obtain the mononuclear fraction using well known techniques. For example, mononuclear cells can be separated from other components of peripheral blood by centrifugation, preferably density gradient centrifugation and most preferably discontinuous density gradient centrifugation. Preferably the mononuclear fraction of the blood sample is separated using a Lymphoprep™ (Axis Shield) density gradient. Thus in some embodiments methods of the invention comprise a preliminary step in which the sample is enriched for mononuclear cells.

As mentioned above, culture of OmniCytes using the serum-free media of the invention for a suitable period of time allows the generation of a population of OmniCyte progeny stem cells. Thus, in a further aspect, the present invention provides a population of stem cells which is referred to herein as "OmniCyte progeny stem cells". In embodiments of any of the aspects disclosed herein, the progeny stem cells are preferably OmniCyte progeny stem cells.

Preferably, in embodiments of any of the aspects disclosed herein, the progeny stem cells have the identifying characteristics of the stem cells having Accession Number P-10-011 of NIBSC/UK Stem cell Bank.

The Examples show the marker expression profile of the OmniCyte progeny stem cell population. FACS analysis of the OmniCyte progeny stem cell population after culture of OmniCytes for 7 days shows that about 35% of the population expressed Oct 4 and about 28% expressed Nanog. About 85% expressed CD45, about 39% expressed CD18, about 37% expressed CD34 and about 16% expressed c-Kit. No significant expression of CD3, CD19 was detected. Immunofluorescence analysis showed that the cell population expressed CD34, CD45, ICAM3, c-Kit, HoxB4, Sox2, Oct4 and Nanog. Thus, a significant percentage of the population of progeny stem cells may express markers selected from Oct-4, Nanog, HoxB4 and Sox-2, more preferably all of these markers. The progeny stem cell population of the invention preferably does not express T and B cell markers such as CD3 and CD19.

Thus, preferably, the population of progeny stem cells of the invention as a whole expresses at least 1 marker selected from Oct-4, Nanog, HoxB4 and Sox-2, more preferably 2 or 3 of these markers, more preferably all of these markers. The expression profile of the cells may be assayed using known methods such as FACS or immunofluorescence.

A reference to a "population as a whole" means that although not every individual member of the population may have the recited feature, at least some members of the population do have the feature, so when the population is analysed, then a positive result is obtained with respect to that feature.

The OmniCyte progeny stem cells of the present invention have a small, lymphocyte-like morphology, i.e. they are small, round mononuclear cells with a high nucleus:cytoplasm ratio.

The OmniCyte progeny stem cell population is characterised by being non-adherent and $CD34^{low}$ or $CD34^{negative}$. This population is also characterised by being obtainable by culturing OmniCytes in the serum-free medium disclosed herein, preferably for at least 24 h, 30, 36, 40, 48, 54, 60, 66 or 72 hours, e.g. about 3-14 days, preferably about 7 days. Preferably, the culture is carried out for no longer than 40, 30, 20, 14, 10, 9 or 8 days.

The progeny stem cells are capable of differentiating into mesodermal, endodermal and ectodermal cell types, for example stomach, colon, liver, pancreas, urinary bladder, urethra, trachea, lung, pharynx, thyroid, parathyroid, intestine, skeletal muscle, bone, epidermis, connective tissue, heart, blood, spleen, central nervous system, lens of the eye, ganglia, nerve, pigment epidermis, hair, and mammary gland cells. Therefore, the progeny stem cells have potential in regenerating wounded or damaged tissue.

The Examples demonstrate that progeny stem cells of the invention have the capacity to repair damaged tissue and/or to inhibit cell death of cells in vitro (FIG. 10) and in vivo (FIG. 11). In both situations, liver cells damaged by thioacetamide (TAA) treatment could be rescued by the progeny stem cells. Liver function was assessed by the expression level of albumin and bilirubin, which is a standard measurement for liver viability. Improved albumin and bilirubin functions were found in rats that received the stem cells, compared to controls. These data shows that the stem cells of the present invention have the capacity to repair damaged liver tissue.

Thus, in a further aspect, there is provided a pharmaceutical composition comprising a population of progeny stem cells of the invention, together with a pharmaceutically acceptable excipient.

In another aspect there is provided a population of progeny stem cells of the invention for use in therapy. In another aspect, there is provided the use of a population of progeny stem cells of the invention for use in the manufacture of a medicament for transplantation therapy, particularly for use in regenerating an organ or repairing a damaged organ. In another aspect, there is provided a method of regenerating an organ or repairing a damaged organ of a patient which comprises administering to said patient progeny stem cells of the invention.

The organ may be selected from the group comprising the immune system, liver, lung, pancreas, bone, cartilage, muscle, skin, brain or nervous system and heart or circulatory system.

For many research or therapeutical applications, it can be advantageous to use genetically modified cells. Thus, any of the methods of the invention may use a genetically modified starting population of stem cells. In embodiments where a genetically modified starting population is used, the progeny will consequently also be genetically modified. Alternatively or in addition, the progeny stem cell may be subjected to genetic modification to yield a population of genetically modified progeny stem cells. Thus, in embodiments of any of the aspects disclosed herein, the progeny stem cell is genetically modified.

Genetic modification may include the introduction of a recombinant nucleic acid molecule into the cell. A recombinant nucleic acid molecule may be introduced into the cell using an expression vector. Methods for introducing nucleic acid molecules into a cell are well known in the art.

The recombinant nucleic acid molecule may encode a gene which is involved in the production of a soluble factor or a cell-surface marker. Preferably, the recombinant nucleic acid molecule encodes a therapeutic factor.

By "recombinant" is meant that the nucleic acid molecule has been introduced into the stem cell. The cell may or may not naturally contain an endogenous copy of the nucleic acid molecule, but it is recombinant in that an exogenous or further endogenous copy of the nucleic acid molecule, e.g. on a vector, has been introduced.

Alternatively or in addition, genetic modification may involve mutating an endogenous gene, for example to create a knock-out of a gene, thereby rendering the cell incapable of expressing said endogenous gene. Examples of genes which may be added recombinantly or which may be knocked out include genes encoding cytokines, prodrugs, cell-surface markers and the like.

Thus, in an embodiment of any of the aspects disclosed herein, the starting stem cell and/or the progeny stem cell contains a recombinant gene and/or it has been genetically modified to contain a knock-out of an endogenous gene.

There is therefore also provided a method of gene therapy, which comprises administration of a genetically modified progeny stem cell to a subject in need thereof.

The inventors also found that at the early stages of the cell culture, the cells are rapidly dividing i.e. a significant proportion of the cells is not in $G_0$-$G_1$, but over a long period of culture using the culture method of the invention, for example several weeks, the cells gradually transit from the S phase to the $G_0$-$G_1$ phase, indicating a trend towards a more quiescent state. For example, after 28 days about 87% of the cells may be in $G_0$-$G_1$. Thus, when it is desired to generate a population of (progeny) stem cells which is rapidly proliferating, the culture methods disclosed herein should be carried out for a short period, e.g. about 7 days, whereas when it is desired to generate a population of (progeny) stem cells in the $G_0$-$G_1$ phase, then culture for a longer period of 3-4 weeks, e.g. about 28 days, should be carried out.

Various documents including, for example, publications and patents, are recited throughout this disclosure. All such documents are, in relevant part, hereby incorporated by reference. The citation of any given document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

It is specifically intended that the above-disclosed optional and preferred features and embodiments of the present invention may be taken alone or together in any number and in any combination, apart from where features or embodiments are mutually exclusive, where it would be impossible to do so or where doing so would be contrary to the aims of the present invention.

The following examples are intended to be illustrative of the present invention and to teach one of ordinary skill in the art to make and use the invention. These examples are not intended to limit the invention in any way. The invention will now be further described in the following Examples and the figures in which:

FIG. 1 is an unsupervised hierarchical clustering heat map of miRNA expression using expression levels (Ct value) of 192 miRNAs, p-value <$10^5$. Higher Ct values correspond to a lower expression level (red colour on the heat map). The Figure shows the results of a micro-RNA analysis using a 466 microRNA chip. The microRNA expression of adherent and non-adherent CD34+ stem cell populations were compared. Several clusters of micro-RNAs and, specifically, group #8 shows a clear difference in expression level between the adherent stem cell populations compared to the control.

FIGS. 2A-2B show (A) a bioinformatic analysis of miR-181a* showing (B) a significant match between the miR-181a* sequence and the 3'UTR Nanog sequence.

FIG. 3 shows the effects of miRNA-181a* mimics and inhibitors on cell proliferation. (A) shows the total viable cell number post-transfection of adherent CD34+ cells with the miR-181a* mimic or inhibitor. (B) shows the absorbance at 450 nm, a measure of cell proliferation of cells treated with either miRNA-181a* mimic or inhibitor or miRNA-21 mimic or inhibitor. Bars represent mean±SD from triplicate wells.

FIGS. 4A-D show (A) the effect of miRNA-181a* mimics and inhibitors on alkaline phosphatase activity. (B) the expression level of Nanog by RT-PCR analysis 72 hours post-transfection of adherent CD34+ cells with the miR-181a* mimic or inhibitor. (C) shows a schematic diagram of the effect of two point mutations on the binding properties of has-miR-181a* using a RNAhybrid program. The two point mutations were generated at cytidine (C)->adenosine (A) as indicated by arrows. (D) Reporter assay of Nanog 3'UTR and mutant Nanog 3'-UTR in cells transfected with the mimic or inhibitor of miR-181a*.

FIG. 5 is a growth curve showing number of viable cells plotted against days of culture. The culture conditions are set out in Example 7.

FIG. 6 shows the morphology of stem cells during culture in serum-free medium of the invention. (a) starting population of CD34+ adherent stem cells; (b) after 24 hours; (c) after 24 hours; (d) after 72 hours; (e) after 14 days.

Figure 9A:
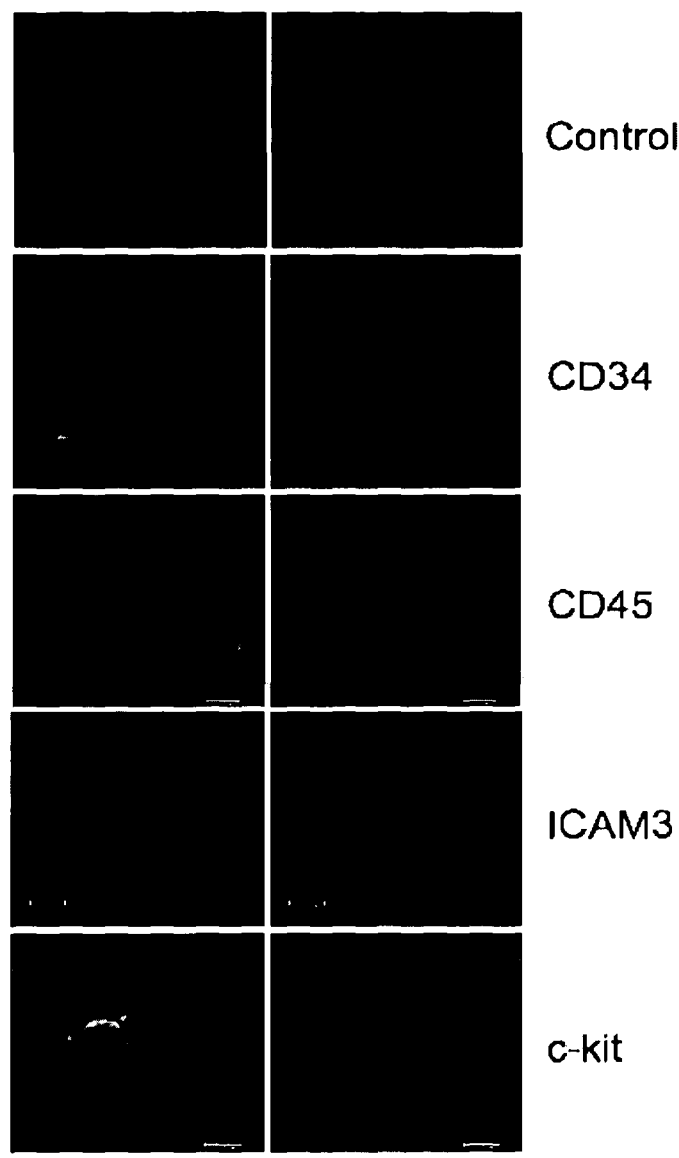
Figure 9:
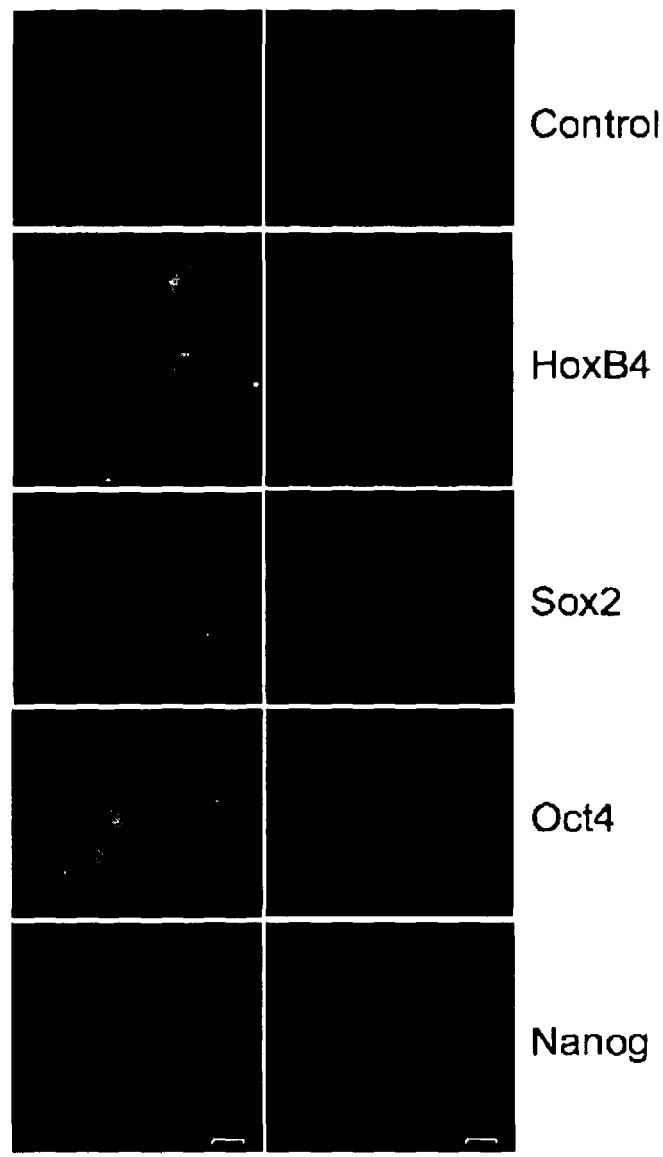

FIGS. 9 (a) and (b) shows the result of immunofluorescence analysis of Example 9.

Figure 10:
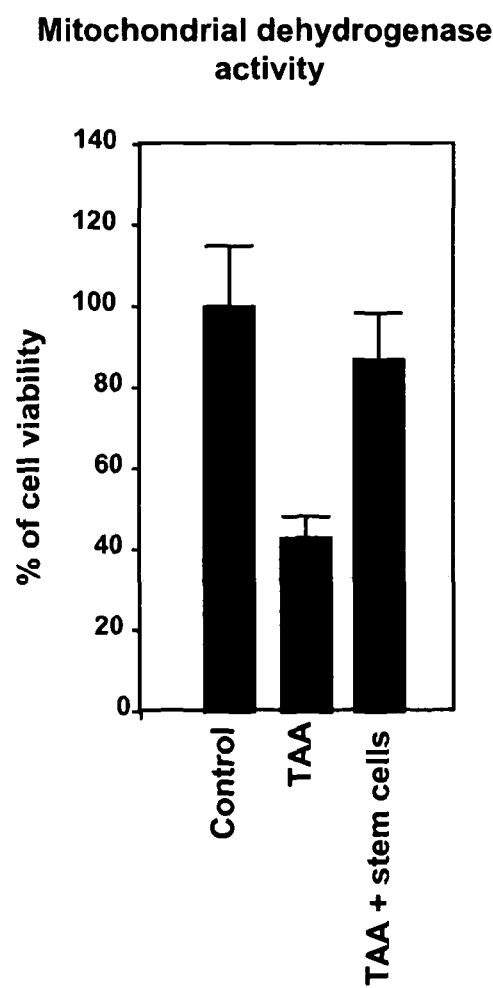

FIG. 10 is a graph showing the results of Example 10a. Enzymatic assay showing cell viability as measured by mitochondrial dehydrogenase activity.

Figure 11:
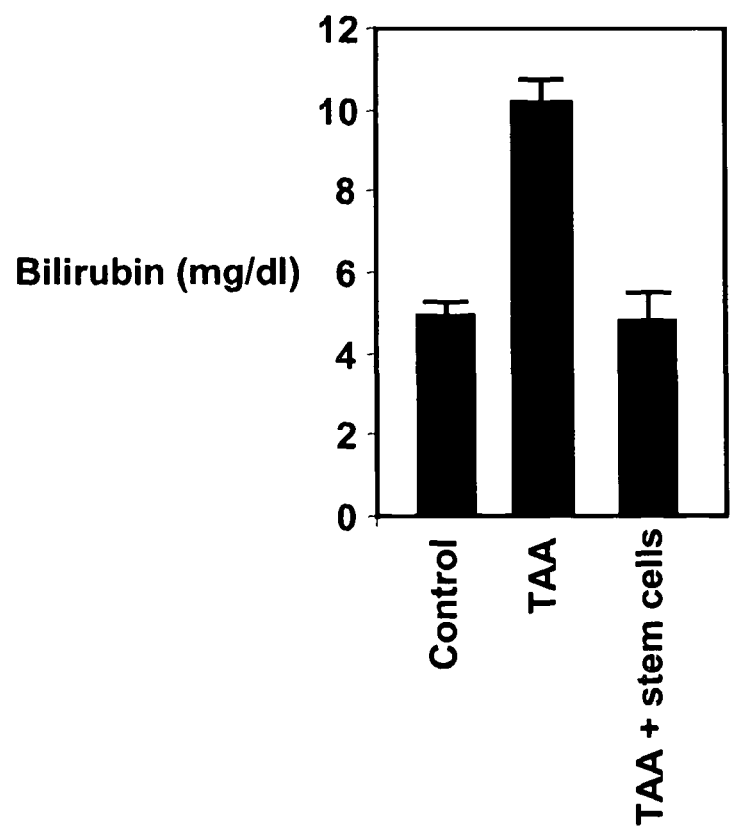

FIG. 11 is a graph showing the results of Example 10b.

EXAMPLES

General Methods
Cell Culture

Normal rat liver cell line CRL-1439 was obtained from American Type Culture Collection (Rockville, USA) and grown in F 12-K or RPMI medium supplemented with 10% fetal bovine serum and 1% penicillin and streptomycin in a 37° C. humidified incubator with 5% $CO_2$. Human normal primary foreskin fibroblast cell line was obtained from the Department of Experimental Haematology at Imperial College London and cultured in RPMI supplemented with 10% fetal bovine serum.

Isolation of Hematopoietic CD34+ Cells and Ex vivo Expansion

Hematopoietic blood samples were obtained with informed patient consent and approved by the local research committee. Samples of granulocyte-colony stimulating factor (G-CSF) mobilised peripheral blood progenitor cells were processed by leukapheresis at the Stem Cell Laboratory at the Hammersmith Hospital. Human mobilised peripheral blood samples were diluted in a ratio of 1:4 in Hanks' buffered saline solution (Gibco, Paisley, UK), the mononuclear cells (MNCs) were separated by centrifugation over a Lymphoprep (Axis-Shield, UK) density gradient at 1800 rpm for 30 minutes. The MNC fraction at the interface was aspirated and washed twice with HBSS, and finally with MACS buffer (phosphate buffered saline solution (DPBS) (Gibco, UK) at pH 7.2 supplemented with 0.5% bovine serum albumin (BSA) and 2 mM EDTA). MNCs were then labelled for CD34+ isolation using CD34+ isolation kit (Miltenyi Biotec, Germany) as described by the manufacturer's protocol using a commercially available human CD34+ MicroBead Kit together with MACS columns and separators. Briefly, $10^8$ mononuclear cells were incubated in 350 µl MACS buffer, 100 µl FcR blocking agent, 50 µl CD34+ magnetic beads at 4° C. for 15 minutes. Labelled cells were then washed in MACS buffer and centrifuged at 1800 rpm for 3 minutes, before being resuspended in 500 µl MACS buffer. Magnetic cell separation was performed using CliniMACS or MiniMACS separation column and a MACS magnetic cell separator. The column was placed in the magnetic field of a suitable MACS separator and washed with 3 ml MACS buffer. The column was removed from the magnetic field and 5 ml of MACS buffer was used to isolate the CD34+ cells. For the expansion, CD34+ cells were added to 24-well or 35 mm tissue-culture treated dish (Nunc, UK) at a density of $2.5\text{-}5\times10^5$ cells in α-MEM medium. After 30 minutes incubation, non-adherent cells were removed and adherent cells were rinsed 3 times with PBS or α-MEM. The adherent CD34+ cell population was expanded in a serum-free condition medium: CellGro serum-free medium (Cellgenix), 250 ng/ml of stem cell factor, 250 ng/ml of interleukin-6, 250 ng/ml of interleukin-3 (Invitrogen or Cellgenix, UK), and 0.5% penicillin/streptomycin antibiotics. Cells were incubated at 37° C. in 5% $CO_2$. Total viable cells were counted using the trypan exclusion assay.

Western Blots

All cell extracts were prepared at a concentration of 60 mg per well in SDS-PAGE loading buffer and loaded onto Novex 12% Tris-Glycine Gels (Invitrogen). Under denaturing conditions, proteins were separated by gel electrophoresis and transferred onto nitrocellulose membrane using a semi-dry blotting apparatus (Trans-Blot SD Semi-Dry, Bio-Rad) or Invitrogen Transblot system (Invitrogen). The membranes were blocked in TBS containing 3% non-fat milk for 1 hour before incubating with primary antibodies for 1 hour at room temperature or overnight in a cold room. Antibodies used were anti-STAT3 (Santa Cruz), anti-pSTAT3 Y705 (Santa Cruz anti-pSTAT3 Ser727 (Santa Cruz), anti-CyclinD1 (New England Biolab), anti-PCNA (New England Biolab), anti-beta actin (Sigma). After subsequent membrane washing, detection was carried out using the appropriate alkaline phosphatase conjugated secondary antibody (1:5000) (Jackson Immuno Research) and incubated for 1 hour at room temperature. Following further washes, proteins were visualised using the BCIP/NTB substrate (Calbiochem).

Example 1

The detailed protocol is described previously [Janowska-Wieczorek et al. (2001) *Stem Cells* 19: 99-107]. Adherent and non-adherent cells were added into a PCR tube and heat treated at 95° C. for 5 min. Then the microRNAs were reverse transcribed into cDNAs by 460 of stem-looped primers. Then these microRNA cDNAs were amplified by 18 cycles of PCR by 460 of forward primers and a universal reverse primer. Finally, the cDNAs were split and individual microRNA was measured by TaqMan probe-directed real-time PCR. All reactions were duplicated. The PCR was done as following by AB7900 with 384-well plates: first, 95° C. for 10 min to activate the Taq polymerase; Then 40 cycles of 95° C. for 15 sec (for denaturation) and 60° C. for 1 min (for annealing and extension). Two replicates were done for each sample. Two independent donor samples were used in the analysis.

Figure 1:
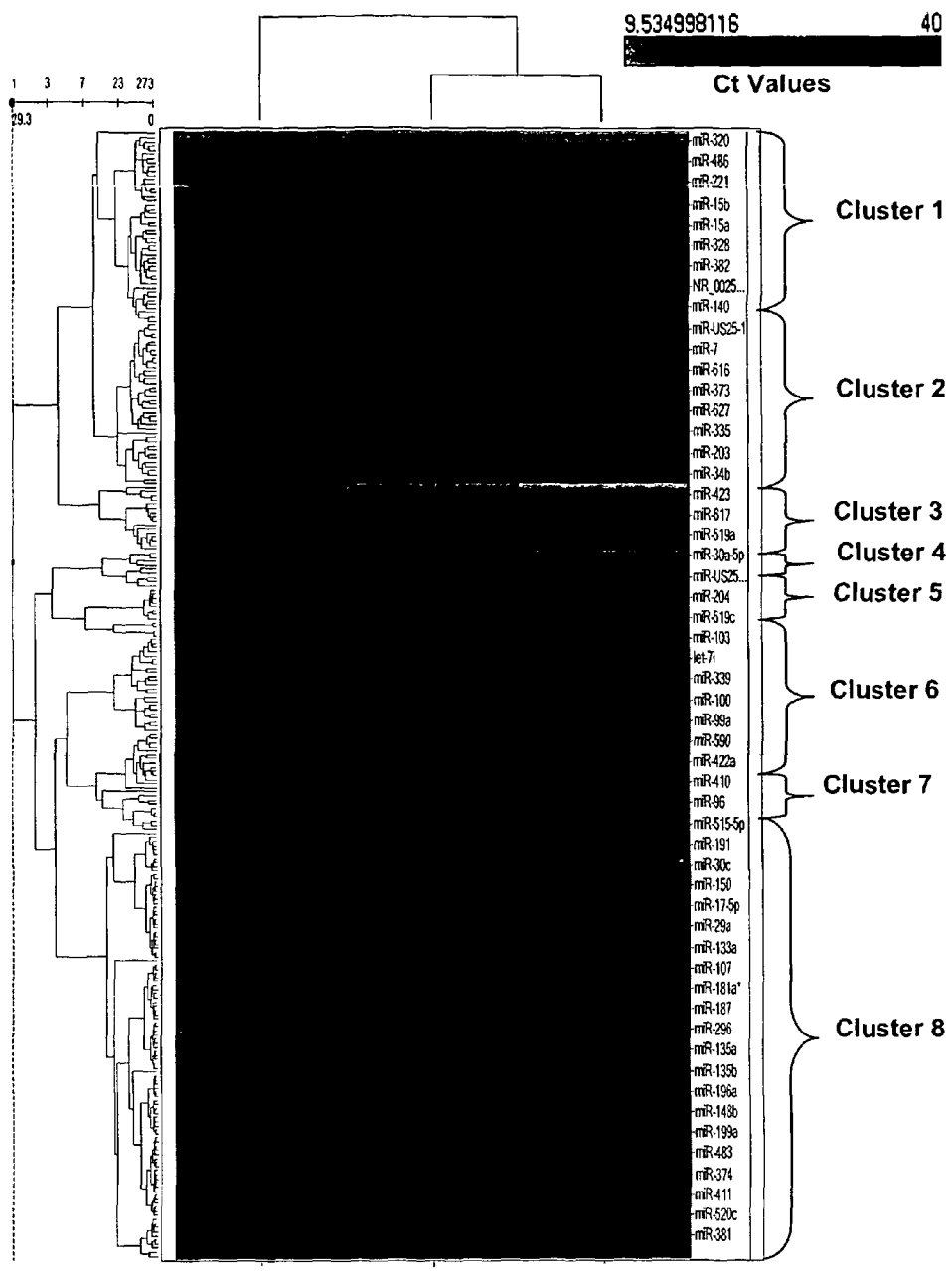

The microRNA expression of adherent and non-adherent CD34+ stem cell populations was compared (FIG. 1). Several clusters of micro-RNAs were identified and, specifically, group #8 shows a clear difference between the adherent stem cell populations compared to the control.

Example 2

Figure 2A:
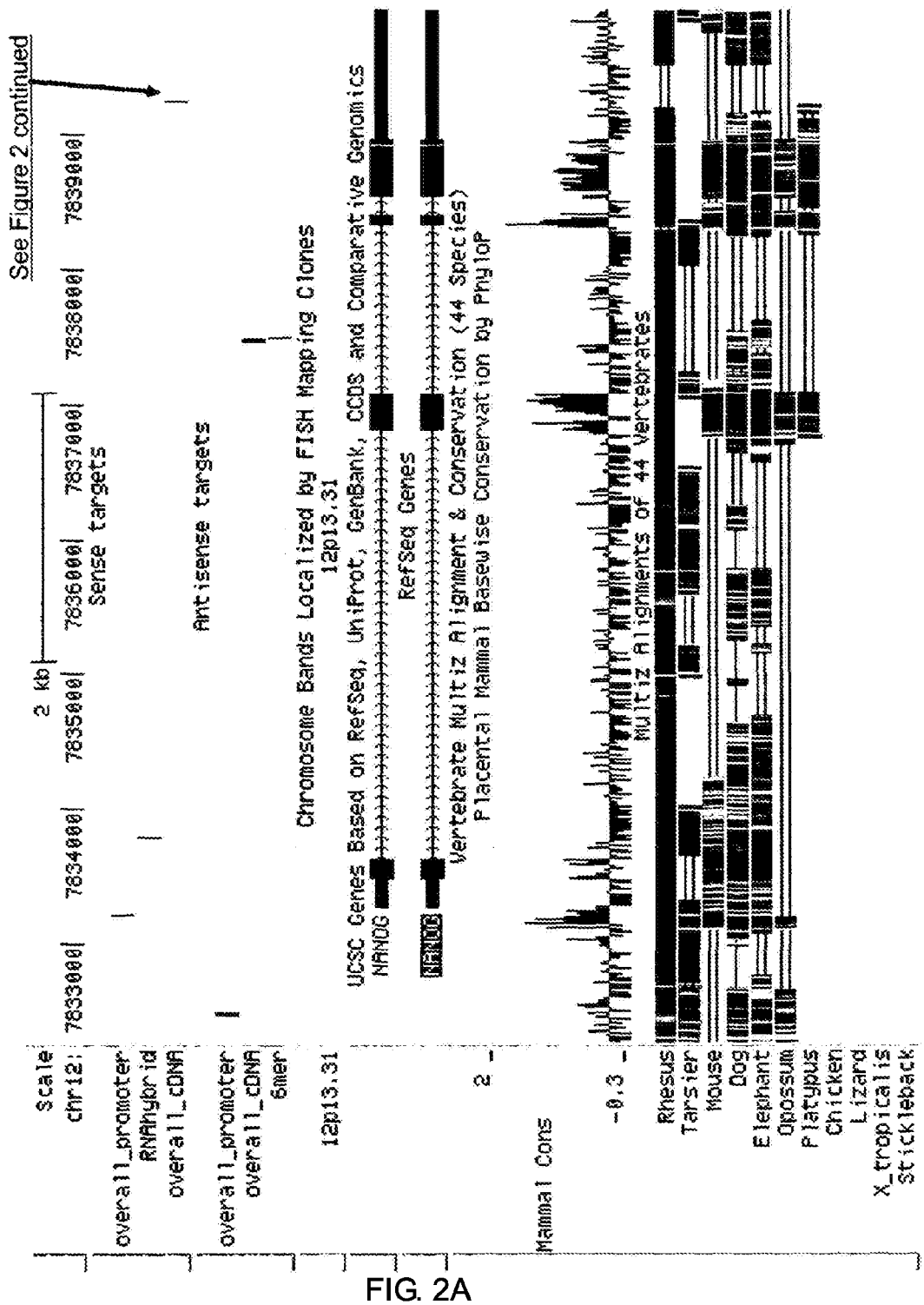

Two of the micro-RNAs identified above, miR-181a* and miRNA-21 were investigated in greater detail. Using bioinformatics, it was found that the miR-181a* targets the 3'UTR of Nanog (FIGS. 2A-2B).

Sequence annotations and data were downloaded from version hg18 of the UCSC table browser's RefSeq Genes track. The genomic loci NANOG, STAT3, HIC1, SOX2, HOXB4, and POU5F1 (Oct4) were scanned for putative target sites for the oligo 5'-ACCAUCGACCGUUGAUUGUACC-3' (SEQ ID NO:3), which corresponds to the star-sequence of hsa-miR-181a. More specifically, the genes' annotated 3' UTR sequences were scanned for (i) seed sites with perfect reverse-complimentarily to the oligo's seed sequence (nucleotides 2-7 from the 5' end) and (ii) sites with strong overall complimentarily to the oligo. Such sites could be target sites for miRNA-like translational suppression and mRNA degradation, and siRNA-like mRNA cleavage. The former scan used a custom python script, whereas the second scan used RNAhybrid with default parameter settings to evaluate potential hybridization between the oligo and target sequence. None of the nine genes' 3' UTRs contained miRNA-like seed sites for the oligo. Of the sites that formed the most stable interactions with the oligo, the NANOG site was the most stable site that contained paired bases at the putative AGO2 cleavage site. The AGO2 cleavage site would presumably be between nucleotides 10 and 11 from the 5' end.

Example 3 miRNA-181a* mimic and inhibitor and miRNA-21 mimic and inhibitor were purchased from Dharmacon. The miRNA-181a* inhibitor used was a single stranded RNA molecule of sequence 5'-gguacaaucaacggucgauggu-3' (SEQ ID NO:4). The miRNA-21 inhibitor used was a single stranded RNA molecule of sequence 5'-ucaacaucagucugauaagcua-3' (SEQ ID NO:6). The miRNA-181a* mimic used was a double-stranded RNA molecule, the guide strand of which having the sequence 5'-accaucgaccguugauuguacc-3' (SEQ ID NO:3). The miRNA-21 mimic used was a double-stranded RNA molecule, the guide strand of which having the sequence 5'-uagcuuaucagacugauguuga-3' (SEQ ID NO:5).

Cell viability/proliferation WST-1 assay was performed. The oligonucleotides were transfected three consecutive times at 50 mM concentration (at day zero, 48 hours, and 72 hours) into approximately $1\times10^5$ progenitor cells in medium containing modified expansion medium (containing 2 ng/ml of SCF, IL-3, and IL-6) using the Nanofectamine reagent (PAA). The WST-1 reagent was used at 1:100 and incubated for one hour. The enzymatic reaction was measured at 450 nm using Bio-Tek ELISA reader.

Figure 3:
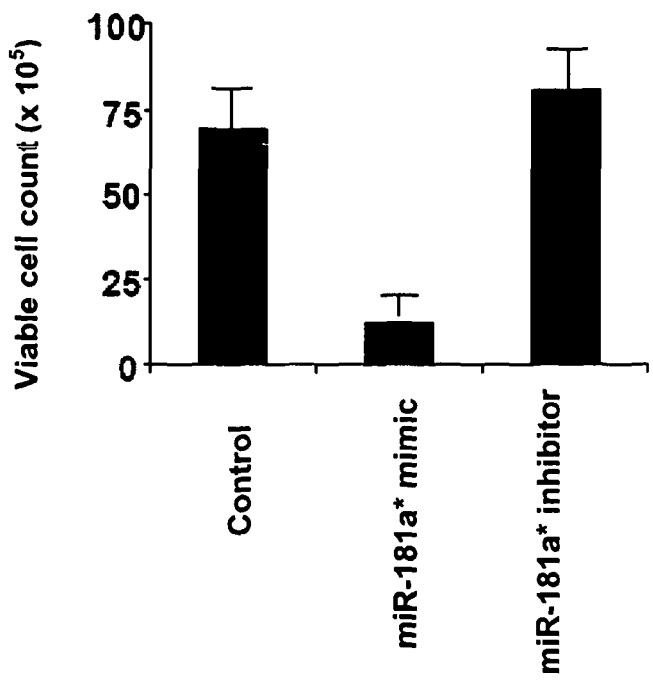
Figure 3:
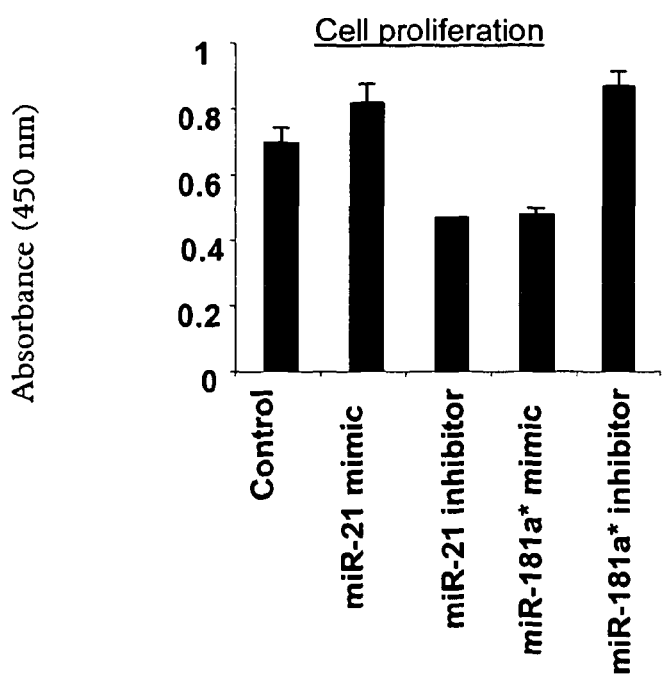

The miRNA-181a* inhibitor was found to increase cell proliferation (FIG. 3B) and the viable cell count (FIG. 3A), whereas the miRNA-181a* mimic had the opposite effect. The miRNA-21 mimic was found to increase cell proliferation (FIG. 3B), whereas the miRNA-21 inhibitor had the opposite effect.

Example 4

The alkaline phosphatase activity level in cells transfected with miRNA-181a* inhibitor and mimic was then assessed. Alkaline phosphatase is a valuable stem cell membrane marker and a higher level of activity is generally associated with a less differentiated state, i.e. a state of increased differentiation potential.

For the alkaline phosphatase assay, approximately $2.5\times10^5$ progenitor cells in 24-wells were transfected two consecutive times with the oligonucleotides (miRNA-181a* inhibitor and mimic as described above) at 100 mM and harvested the cells 72 hours post-transfection as described in the alkaline phosphatase assay kit (Cell Biolabs). Equal protein load at 100 μg of protein was used for the assays and the reaction was measured after 1 hour incubation at 37° C. at 405 ηm in an ELISA reader.

Figure 4A:
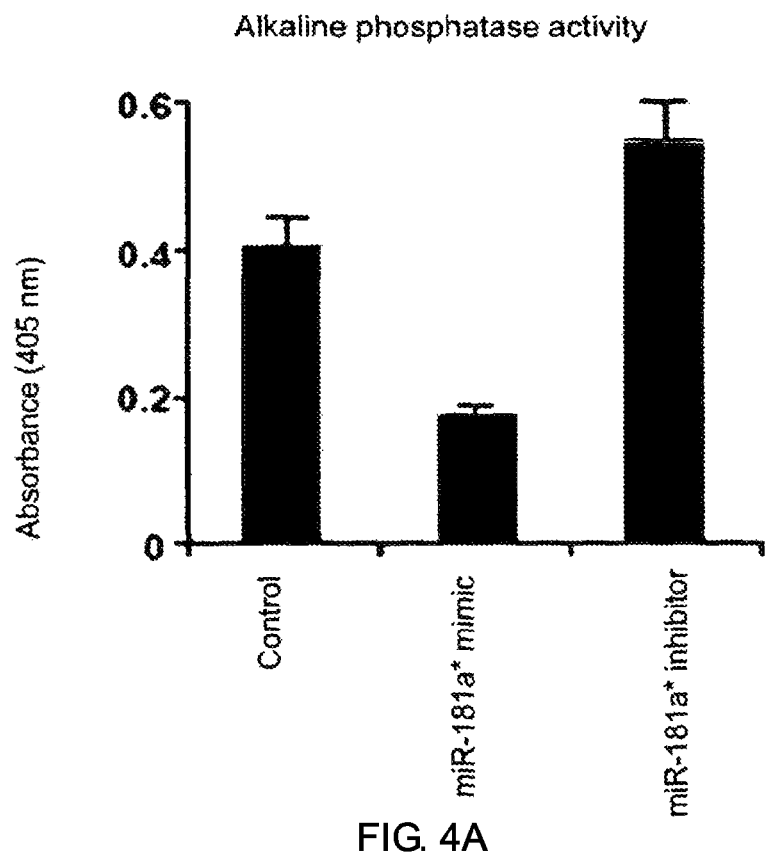

Cells transfected with miRNA-181a* inhibitor showed an increased level of alkaline phosphatase activity compared to the control, whereas cells transfected with miRNA-181a* mimic showed a reduced level of alkaline phosphatase activity compared to the control (FIG. 4A).

Example 5

Nanog is known to be a significant factor in stem cell self-renewal. It was therefore investigated whether a miR-181a* mimic and inhibitor would have any affect on the Nanog expression level.

The miRNA 181a* mimic and inhibitor as described above were purchased from Dharmacon. The oligonucleotides were transfected (at day zero and again at 24 hours) at 100 mM into 1×105 adherent CD34+ stem cells using the Nanofectamine reagent following the manufacturer's recommendation (PAA). Total RNA was harvested post-transfection at 72 hours in addition to counting the total cell numbers by trypan exclusion assay (pooled from three wells). Total RNA was recovered using the RNAqueous-Micro kit (Ambion) following the manufacturer's recommendation. The RNA was quantified using a Nanodrop 2000 micro-sample quantitator. 500 ng of total RNA from each sample was reverse transcribed using the One Step RT-PCR kit from Qiagen following the manufacturer's recommendation. Expression of human Nanog was measured semi-quantitatively by PCR using primer pair from R&D systems after 32 cycles at 94° C. for 45 sec. 55° C. for 45 sec. and 72° C. for 45 sec. GAPDH primers: Forward (5'-GTGAAGGTCGGAGTCAACG-3' (SEQ ID NO:7)) and Reverse (5'-GGTGAAGACGCCAGTG-GACTC-3' (SEQ ID NO:8) was used as a loading control after 30 cycles at 94° C. for 45 sec. 60° C. for 45 sec. and 72° C. for 1 min. The samples were separated on agarose gel and analysed using UVP Geldoc system (UVP, UK).

Figure 4B:
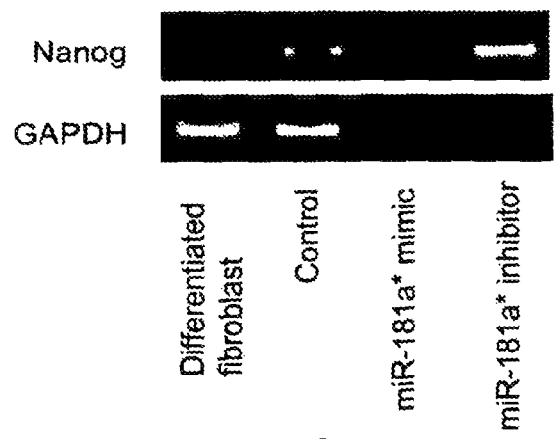

It was found that the mimic down regulates the Nanog expression, whereas the inhibitor up-regulates it (FIG. 4B).

Example 6

Figure 4C:
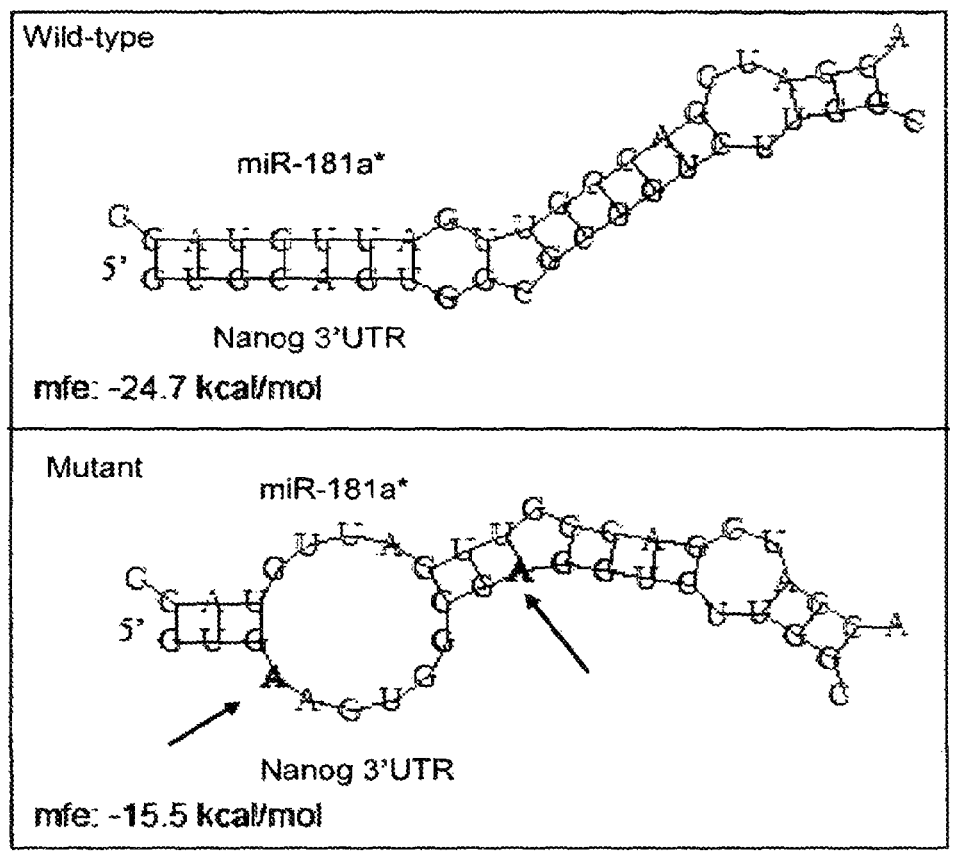

To determine whether miR-181a* targets the Nanog 3'UTR, we generated luciferase reporters that have either the wild-type or a mutant containing two point mutations at cytidine (C) to adenosine (A) substitution as shown by arrows (FIG. 4C).

Nanog 3' UTR was amplified from genomic DNA (HeLa) by nested PCR using two different forward primers and a single reverse primer (primers are listed below). For both PCRs, 50 µl sample volumes were prepared using 0.3 µM each of Forward and Reverse primers, 1× Accuprime™ Pfx Reaction Mix (Invitrogen), and 1.0 unit of Accuprime™ Pfx DNA Polymerase (Invitrogen). 100 ng of genomic DNA and 0.5 µl of PCR product were used as templates in the first and the second PCR, respectively. The Forward 2 and the Reverse primers each contained two restriction enzyme cut sites; XhoI and SgfI for Forward 2 and NotI and EcoRI for Reverse. The Nanog 3' UTR construct was cloned into the psiCHECK™ 2.2 vector (Promega), using the unique restriction enzyme cut sites for NotI and XhoI. The Nanog 3' UTR insert, 960 bp in length, was verified by sequencing. Site-specific point mutations in the target site of hsa-miR-181a*. Two point mutations were inserted in the Nanog 3'UTR target site of hsa-miR-181a* using two mutagenic primers and psiCHECK™ 2.2 with Nanog 3' UTR insert as template. A 25.5 µl PCR sample volume was prepared using 10 ng of template, 0.5 µM of each primer, 1×Reaction buffer (Stratagene), dNTP mix (0.2 µM each, Finnzymes), and 1.25 units of PfuTurbo DNA polymerase (Stratagene). The mutant Nanog 3' UTR was verified by sequencing. Sequence of hsa-miR-181a* target site (wt): GTGCAGTGGCGCGGTCTTGGC (SEQ ID NO:9). Sequence of mutated hsa-miR-181a* target site (mutations shown in bold and underlined): GTGAAGTGGCGAGGTCTTGGC (SEQ ID NO:10). List of primer sequences: Forward 1, AGCAACCAGACCCAGAACATCCAG (SEQ ID NO:11); Forward 2, GCGATCGCTCGAGAGATGAGT-GAAACTGATATTACTCAATTTCAGTCTGG (SEQ ID NO:12); Reverse, GAATTCGCGGCCGCATGTTTAAGCT-GTATATTTACTCATTGAAACACTCGG (SEQ ID NO:13); psiCHECK+, AGGACGCTCCAGATGAAATG (SEQ ID NO:14); Nanog seq, TCACTGCAAGCTCCGTCTCC (SEQ ID NO:15); Rev psiCHECK, CAAACCCTAACCAC-CGCTTA (SEQ ID NO:16); Nanog Mut F, GGCTGGAGT-GAAGTGGCGAGGTCTTGGCTC (SEQ ID NO:17); Nanog Mut R, GAGCCAAGACCTCGCCACTTCACTC-CAGCC (SEQ ID NO:18).

For the reporter luciferase reporter assay, 100 nM of miR181a* mimic or inhibitor as described above (Dharmacon) were transfected into CD34 progenitor cells (2.5×10⁵ cells/well) in a 24 well plate for 24 hours. The Nanog 3'UTR wild-type or mutant with two point mutations were cloned downstream of the *Renilla* translational stop codon in psiCHECK-2 vector (Promega) as described above. 100 ng of the 3-UTR-Nanog (3-UTR-Nanog-psi-CHECK-2) or its mutated variant was co-transfected into the cells pre-conditioned with miR181a* mimic or inhibitor for further 24 hours before harvesting. Empty (psiCHECK-2) vector was used for normalisation and 3-UTR-Nanog alone was used as a control. *Renilla* and Firefly luciferase assay was carried out using the Dual-Luciferase Reporter Assay System (Promega) following the manufacturer's instructions. Readings were measured using a luminometer (Perkin-Elmer VICTOR). The ratio of *Renilla* luciferase level (RL) relative to firefly luciferase from the empty vector (psiCHECK-2) was normalised to 1.0 and compared with RL from the other conditions.

Figure 4D:
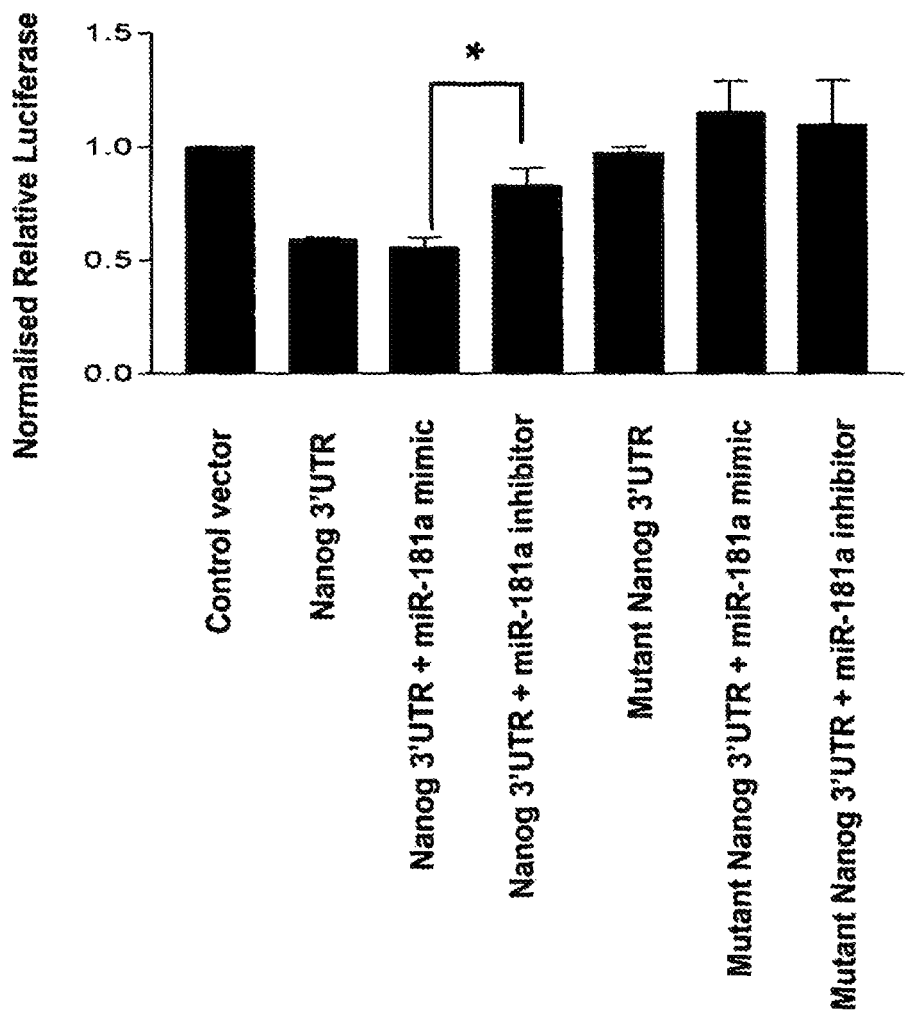

Cells transfected with the mimic pre-miR-181a* along with the wild-type Nanog 3' UTR suppress the luciferase activity, whereas the anti-miR-181a* partially increased the activity (FIG. 4D). The mutant Nanog 3' UTR did not affect the reporter activities (FIG. 4D). These studies indicate that miRNA-181a* targets the Nanog 3'-UTR.

Example 7

Ex vivo Culture of Stem Cells

Figure 5:
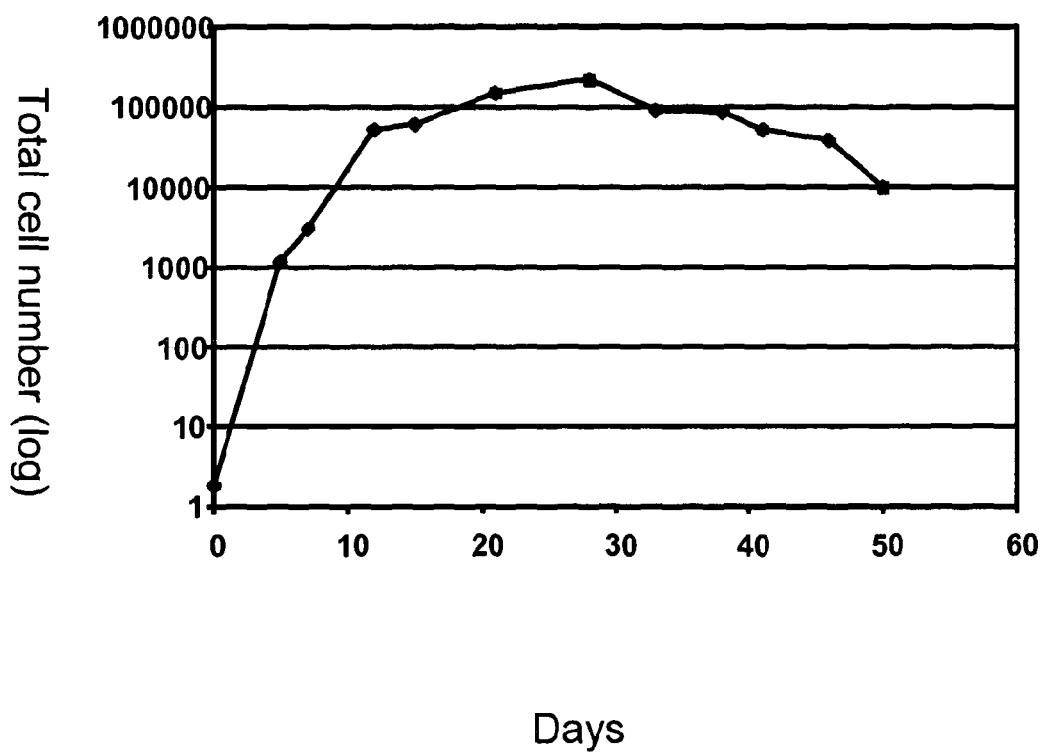
Figure 6:
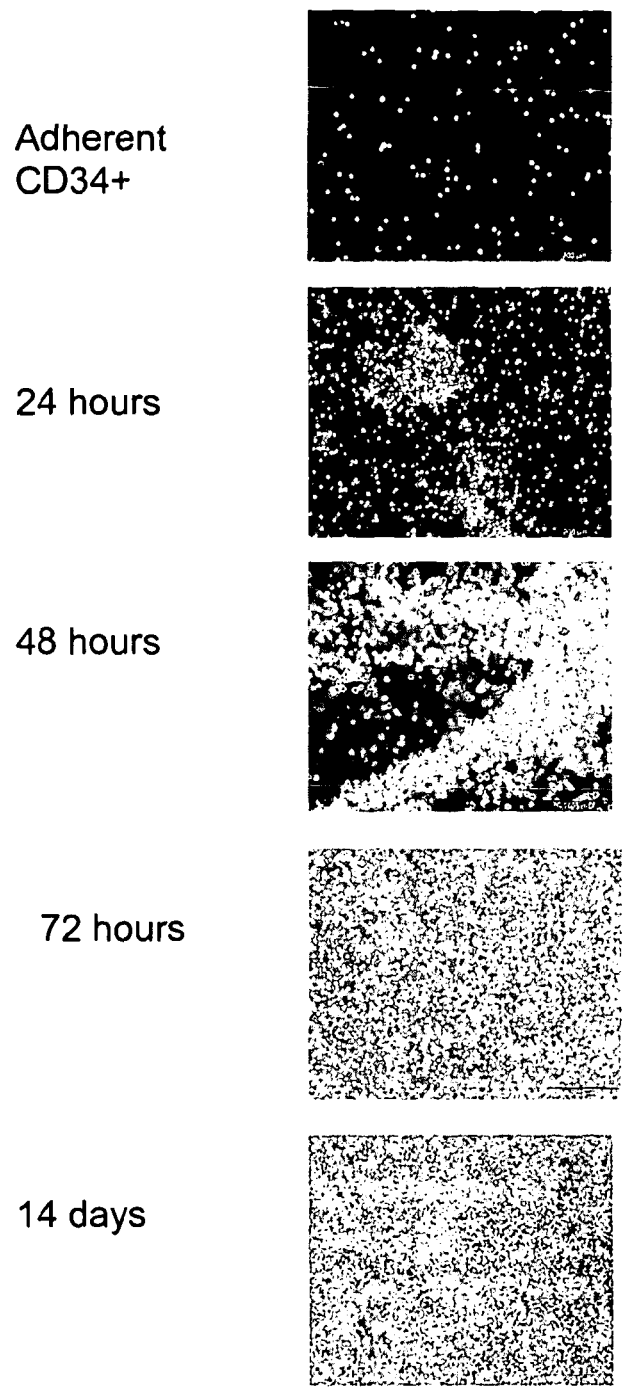

The following conditions were established to be optimal for culture of stem cells such as CD34+ adherent stem cells (e.g. OmniCytes): Serum-free medium such as Cellgro serum-free GMP grade medium (Cellgenix, UK), supplemented with SCF at 250 ng/mL, IL-3 at 250 ng/mL, and IL-6 at 250 ng/ml. Cells were incubated at 37° C. in 5% $CO_2$. For the growth curve analysis, the medium was changed every $7^{th}$ day and the total viable cells were counted by trypan exclusion assay. Results are shown in FIG. 5. The morphology of the cells from days 0 to 14 is shown in FIG. 6.

Example 8

Cell Cycle Analysis

Figure 7:
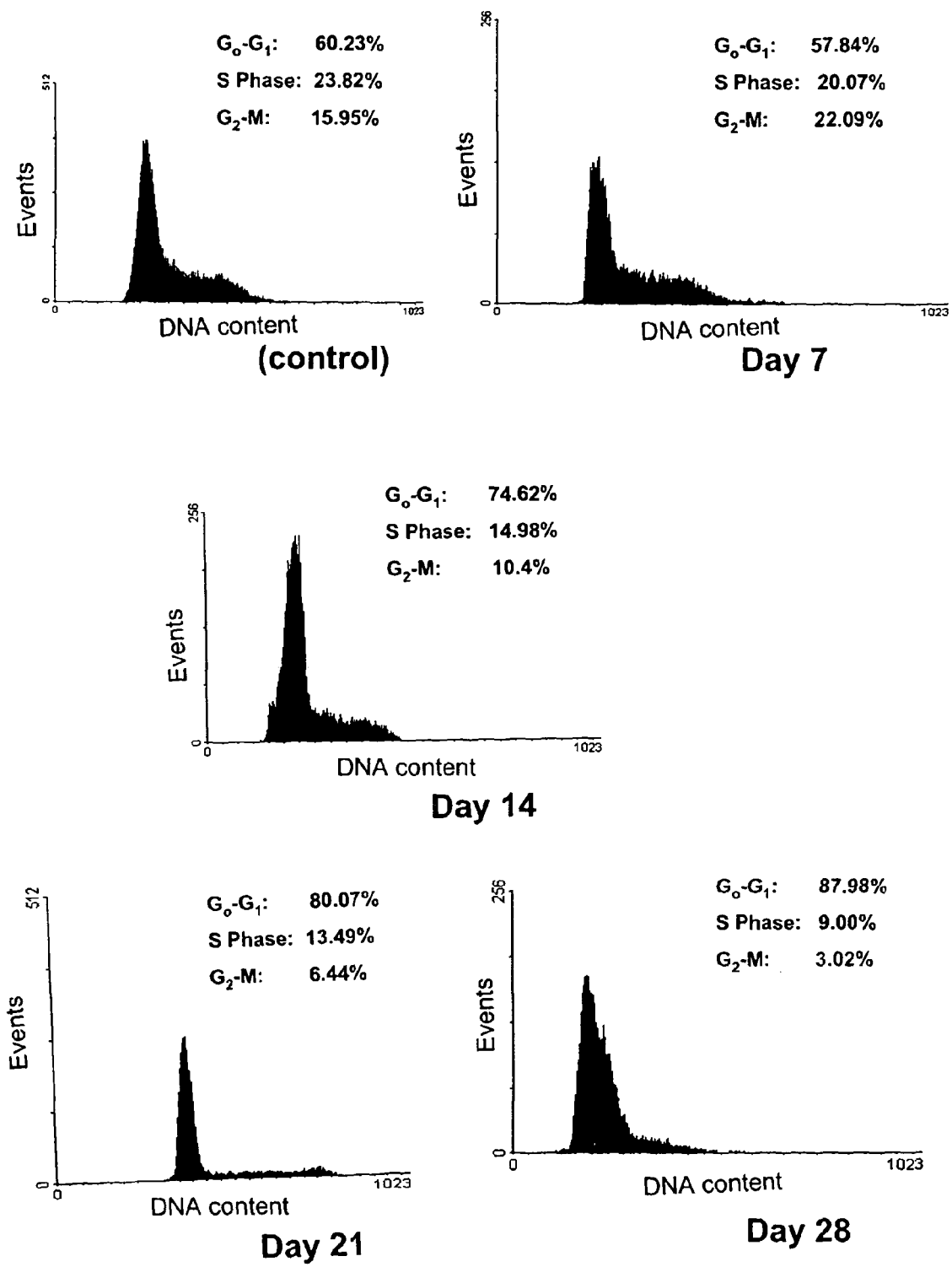
FIG. 7 shows the results of FACS analysis of the cell cycle analysis during stem cell culture in serum-free medium (Example 8).
Figure 8A:
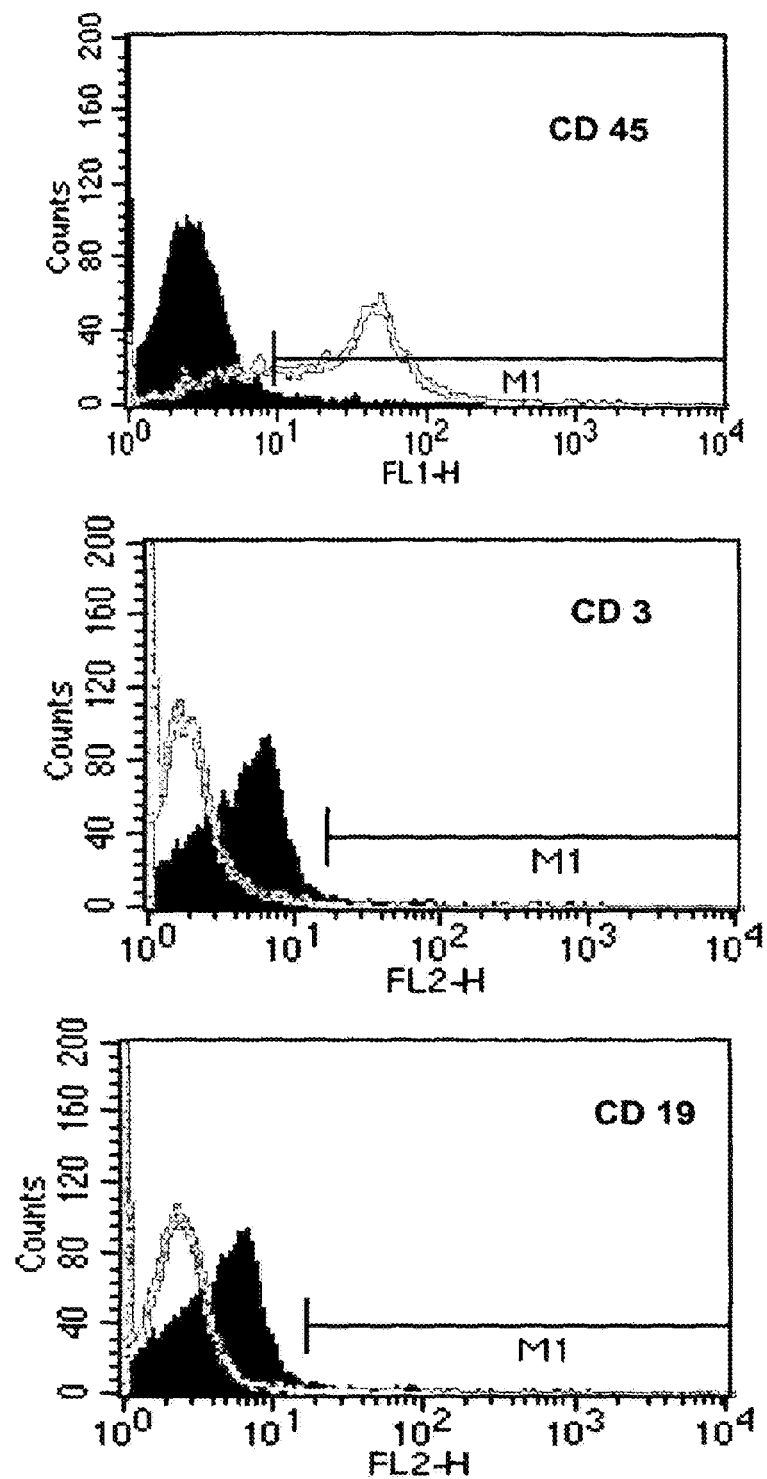
FIGS. 8A-8C show the results of flow cytometry analysis of Example 9.
Figure 8B:
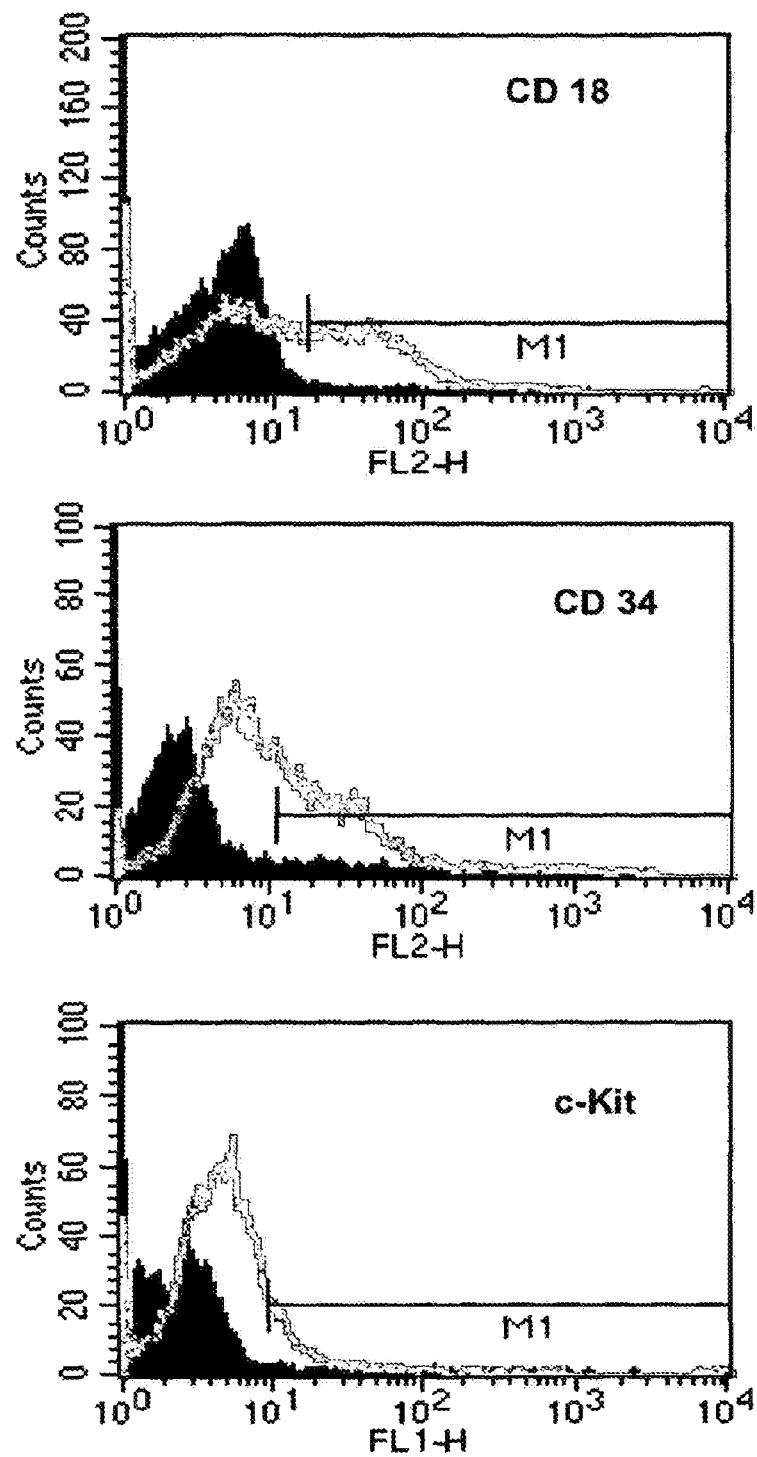
Figure 8C:
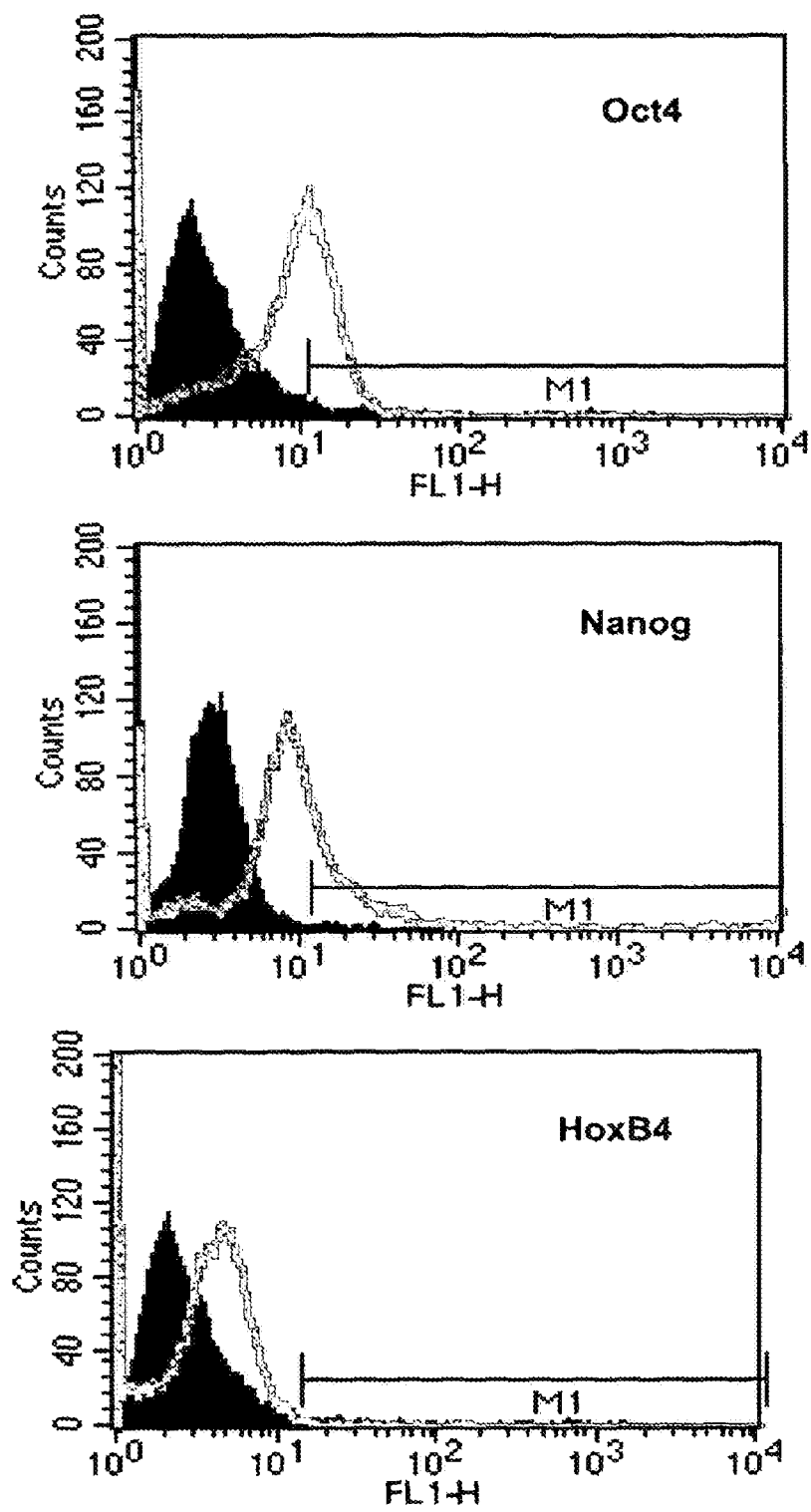

Cells cultured according to Example 7 were fixed in 70% ice-cold ethanol in PBS and kept on ice for 1 hour. Following thorough washing with PBS, cells were re-suspended in 1 ml of PBS. 100 μg/ml RNase (Sigma, UK) and 40 μg/ml Propidium Iodide (Sigma) were added and cells were incubated for 1 hour at 37° C. Next, cells were washed in PBS and re-suspended in 250 μl PBS for analysis by FACScalibur flow cytometer (Becton Dickinson, San Jose, Calif., USA). The DNA profile of the cells was read at the FL2 channel in order to distinguish between the $G_0$-$G_1$, S and $G_2$-M phases of the cell cycle. Results are shown in FIG. 7.

Example 9

Marker Expression Analysis (a) Flow Cytometry

Stem cells obtained according to the method described above were cultured according to Example 7 for 7 days. After 7 days, approximately $1 \times 10^5$ cells were stained and analyzed per sample. For cell surface markers no permeabilisation was used and primary antibody was added to each tube at a dilution of 1:50 for 20 minutes at room temperature. Three washes were performed with PBS. Secondary antibody, conjugated to FITC, PE or APC was added at 1:100 and incubated at room temperature in for 20 minutes. Secondary antibody was washed with PBS. The cells were resuspended in 200 μl of PBS prior to analysis. For intracellular staining, the cells were fixed and permeabilised using Fix & Perm® kit (Invitrogen, USA) before adding primary antibody. Primary antibody was added into the Perm solution and left to incubate for 20 minutes at room temperature. Each tube was washed and stained with secondary antibody as mentioned above.

Isotype-matched controls were used for each antibody stained. Analysis of the labeled cells was performed with a FACScalibur flow cytometer (Becton Dickinson, San Jose, Calif., USA). Approximately, 10,000 cells were aimed to be collected for each test sample to ensure a sufficient number of positive stained cells. Results are shown in FIGS. 8A-8D, which show that about 35% of the population expressed Oct 4 and about 28% expressed Nanog. About 85% expressed CD45, about 39% expressed CD18, about 37% expressed CD34 and about 16% expressed c-Kit. No significant expression of CD3, CD19 was detected.

(b) Immunofluorescence

Stem cells obtained according to the method described above were cultured according to Example 7 for 7 days. After 7 days, cells were fixed in 4% formaldehyde (20 minutes) without permeablisation followed by 2 washes with PBS. The fixed cells were air dried onto glass coverslips prior to use. The cells were blocked with normal donkey serum for 30 minutes prior to adding primary antibodies for cell surface markers CD34, CD45, c-kit, and ICAM3. The labelled cells were incubated for 2 hours at room temperature and washed 3 times with TBS. Secondary antibodies were added (1:200) and incubated fro 1 hour at room temperature. Three washes were performed and the cells were mounted with vector shield hard mount containing DAPI and analysed using a fluorescent Leica DM4000 microscope. For intracellular localisation of stem cell markers, the cells were permeabilised with 0.2% Triton X100 after fixing in 4% formaldehyde. The following stem cell markers were used: HoxB4, Sox2, oct4, and Nanog. All the antibodies used were diluted at 1:10 prior to labelling.

Results are shown in FIG. 9, which shows that the cell population expressed CD34, CD45, ICAM3, c-Kit, HoxB4, Sox2, Oct4 and Nanog.

Example 10

Therapeutic Effects of Cultured Stem Cells—TAA Biological Assay

In vitro Study

Normal rat liver cells (40,000) per well were seeded on the bottom chamber of 12-well Transwell plates. The liver cells were cultured in RPMI medium and incubated overnight in a tissue culture incubator. The cells were washed with PBS followed by adding 300 ul of IMDM serum-free medium to the bottom chamber. The upper chambers contained (i) 300 μl of the control medium (IMDM medium containing each 250 ng/ml of SCF/IL-3/IL-6); or
(ii) control medium+TAA (thioacetamide, 50 mM); or
(iii) control medium+TAA+7 day cultured stem cells ($1 \times 10^5$ cells) cultured according to Example 7. The liver cells were incubated for 17 hours followed by removal of the upper chamber. Liver cell viability WST-1 assay was performed. The WST-1 reagent was used at 1:100 and incubated for 30 minutes. The enzymatic reaction (expressed as mitochondrial dehydrogenase activity) was measured at 450 nm using Bio-Tek ELISA reader. Cell morphological analysis was done on an Olympus microscope.

Results are shown in FIG. 10 which shows the beneficial effect of the cultured stem cells (OmniCyte progeny stem cells).

In vivo TAA Study.

The animal studies were approved by the local research committee. Rats were exposed to the hepatotoxin TAA at 350 mg/Kg body weight, which induces liver damage. Three groups (7 rats per group) were in the study: group 1 (control group, no TAA), group 2 (TAA treated), and group 3 (TAA treated followed by treatment with 7 day cultured stem cells according to Example 7). The animals were treated for two consecutive days followed by immunosuppressant treatment at 0.5 mg per 100 g rat. The following day the rats were injected with $2 \times 10^7$ cultured stem cells per rat. After 24 hour treatment, liver tissues and blood samples were taken from all the three groups for analysis. Liver functions were assayed by measuring bilirubin and albumin levels (BioAssay Systems, USA).

Results are shown in FIG. 11 which shows the beneficial effect of the cultured stem cells (OmniCyte progeny stem cells).

The invention claimed is:

1. An in vitro method of maintaining the differentiation potential of a population of stem cells, said method comprising contacting said cells with an inhibitor which inhibits miRNA-181a* (SEQ ID NO:3), wherein the inhibitor which inhibits miRNA-181a* is a RNA molecule comprising a sequence which has at least 95% complementarity to the miRNA-181a* guide strand sequence of SEQ ID NO:3.

2. The method of claim 1 comprising culturing the cell population in a culture medium which is serum free and comprises stem cell factor (SCF), Interleukin-3 (IL-3) and Interleukin 6 (IL-6).

3. The method of claim 2 wherein the culture medium further comprises interleukin-1.

4. The method of claim 1, wherein the cell population is selected from the group consisting of haematopoietic stem cells, mesenchymal stem cells and induced pluripotent stem cells (iPSCs).

5. The method of claim 1, wherein the cell population is CD34+.

6. The method of claim 1, wherein the cell population is pluripotent, capable of self-regeneration and able to adhere to plastic during culturing.

7. The method of claim 1, wherein the cell population is obtainable by:
   i) subjecting haematopoietic tissue to density gradient separation;
   ii) exposing low density cells to an affinity ligand for CD34;
   iii) recovering cells attached to said CD34 ligand;
   iv) exposing the CD34+ subpopulation to tissue culture grade plastic; and
   v) recovering CD34+ cells adherent to the plastic.

8. The method of claim 1, wherein the cell population has defining characteristics of cells deposited with ECACC at Porton Down, Salisbury, SP4 OJG on 24 Sep. 2004 under accession number 04092401.

9. The method of claim 1 wherein the inhibitor which inhibits miRNA -181a* (SEQ ID NO:3) is a single or double stranded short RNA molecule and comprises a first strand of 12 to 50 nucleotides in length.

10. The method of claim 9 wherein said first strand comprises or consists of sequence GGUACAAUCAACGGUCGAUGGU (SEQ ID NO:4).

11. The method of claim 9 wherein said first strand is 22 nucleotides in length.

12. The method of claim 1, further comprising contacting said cells with an inhibitor of signal transducer and activator of transcription 3 (STAT 3).

13. The method of claim 1, further comprising contacting said cells with an inhibitor of miRNA21.

14. A serum-free medium suitable for culturing stem cells, said serum-free medium comprising Interleukin-3, Interleukin-6 SCF and an inhibitor which inhibits miRNA -181a* (SEQ ID NO:3), wherein the inhibitor which inhibits miRNA-181a* is a RNA molecule comprising a sequence which has at least 95% complementarity to the miRNA-181a* guide strand sequence of SEQ ID NO:3.

15. A method of generating a population of progeny stem cells, comprising contacting a stem cell population which is CD34+, capable of adhering to plastic and capable of differentiation into endodermal, ectodermal and mesodermal cell types with serum-free medium according to claim 14, and incubating said stem cell population for a suitable length of time, thereby generating a population of progeny stem cells.

16. The method according to claim 15, wherein said progeny stem cell population is non-adherent and $CD34^{low}$ or $CD34^{negative}$.

17. The method according to claim 15, wherein said progeny stem cell population expresses CD45, ICAM3, c-Kit, HoxB4, Sox2, Oct4 and/or Nanog.

18. The method according to claim 15, wherein said progeny stem cell population is capable of differentiation into endodermal, ectodermal and mesodermal cell types.

19. The method according to claim 15, wherein the method comprises
(i) subjecting haemopoietic tissue to density gradient separation;
(ii) exposing low density cells to an affinity ligand for CD34;
(iii) recovering cells attached to said CD34 ligand;
(iv) exposing the $CD34^+$ subpopulation to tissue culture grade plastic;
(v) recovering $CD34^+$ cells adherent to the plastic; and
(vi) incubating the CD34+ adherent cells in said serum-free medium.

20. The method of claim 9 wherein the inhibitor which inhibits miRNA -181a* (SEQ ID NO:3) comprises a second strand of 12 to 50 nucleotides in length.

21. The method of claim 20 wherein the inhibitor which inhibits miRNA -181a* (SEQ ID NO:3) is a double stranded RNA molecule which consists of the first strand and the second strand base-paired together with one or more unpaired nucleotides at the 3' end of each strand forming 3' overhangs.

* * * * *

SEQUENCE LISTING

```
<160> NUMBER OF SEQ ID NOS: 18

<210> SEQ ID NO 1
<211> LENGTH: 110
<212> TYPE: RNA
<213> ORGANISM: Artificial Sequence
<220> FEATURE:
<223> OTHER INFORMATION: RNA
```

-continued

<400> SEQUENCE: 1
ugaguuuuga gguugcuuca gugaacauuc aacgcugucg gugaguuugg aauuaaaauc    60
aaaaccaucg accguugauu guacccuaug gcuaaccauc aucuacucca              110

<210> SEQ ID NO 2
<211> LENGTH: 23
<212> TYPE: RNA
<213> ORGANISM: Artificial Sequence
<220> FEATURE:
<223> OTHER INFORMATION: RNA

<400> SEQUENCE: 2
aacauucaac gcugucggug agu                                           23

<210> SEQ ID NO 3
<211> LENGTH: 22
<212> TYPE: RNA
<213> ORGANISM: Artificial Sequence
<220> FEATURE:
<223> OTHER INFORMATION: RNA

<400> SEQUENCE: 3
accaucgacc guugauugua cc                                            22

<210> SEQ ID NO 4
<211> LENGTH: 22
<212> TYPE: RNA
<213> ORGANISM: Artificial Sequence
<220> FEATURE:
<223> OTHER INFORMATION: RNA

<400> SEQUENCE: 4
gguacaauca acggucgaug gu                                            22

<210> SEQ ID NO 5
<211> LENGTH: 22
<212> TYPE: RNA
<213> ORGANISM: Artificial Sequence
<220> FEATURE:
<223> OTHER INFORMATION: RNA

<400> SEQUENCE: 5
uagcuuauca gacugauguu ga                                            22

<210> SEQ ID NO 6
<211> LENGTH: 22
<212> TYPE: RNA
<213> ORGANISM: Artificial Sequence
<220> FEATURE:
<223> OTHER INFORMATION: RNA

<400> SEQUENCE: 6
ucaacaucag ucugauaagc ua                                            22

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gtgaaggtcg gagtcaacg                                                19

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggtgaagacg ccagtggact c                                            21

<210> SEQ ID NO 9
<211> LENGTH: 21
<212> TYPE: DNA
<213> ORGANISM: Artificial Sequence
<220> FEATURE:
<223> OTHER INFORMATION: MicroRNA Target Site

<400> SEQUENCE: 9
gtgcagtggc gcggtcttgg c                                            21

<210> SEQ ID NO 10
<211> LENGTH: 21
<212> TYPE: DNA
<213> ORGANISM: Artificial Sequence
<220> FEATURE:
<223> OTHER INFORMATION: MicroRNA Target Site

<400> SEQUENCE: 10
gtgaagtggc gaggtcttgg c                                            21

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
agcaaccaga cccagaacat ccag                                         24

<210> SEQ ID NO 12
<211> LENGTH: 50
<212> TYPE: DNA
<213> ORGANISM: Artificial Sequence
<220> FEATURE:
<223> OTHER INFORMATION: Primer

<400> SEQUENCE: 12
gcgatcgctc gagagatgag tgaaactgat attactcaat ttcagtctgg             50

<210> SEQ ID NO 13
<211> LENGTH: 51
<212> TYPE: DNA
<213> ORGANISM: Artificial Sequence
<220> FEATURE:
<223> OTHER INFORMATION: Primer

<400> SEQUENCE: 13
gaattcgcgg ccgcatgttt aagctgtata tttactcatt gaaacactcg g           51

<210> SEQ ID NO 14
<211> LENGTH: 20
<212> TYPE: DNA
<213> ORGANISM: Artificial Sequence
<220> FEATURE:
<223> OTHER INFORMATION: Primer

```
<400> SEQUENCE: 14
aggacgctcc agatgaaatg                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tcactgcaag ctccgtctcc                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caaaccctaa ccaccgctta                                              20

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
ggctggagtg aagtggcgag gtcttggctc                                   30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gagccaagac ctcgccactt cactccagcc                                   30
```